(12) United States Patent
Mirkin et al.

(10) Patent No.: US 8,507,200 B2
(45) Date of Patent: Aug. 13, 2013

(54) PARTICLES FOR DETECTING INTRACELLULAR TARGETS

(75) Inventors: Chad A. Mirkin, Wilmette, IL (US); Dwight Seferos, Toronto (CA); David A. Giljohann, Chicago, IL (US)

(73) Assignee: Northwestern University, Evanston, IL (US)

( * ) Notice: Subject to any disclaimer, the term of this patent is extended or adjusted under 35 U.S.C. 154(b) by 591 days.

(21) Appl. No.: 12/526,560

(22) PCT Filed: Feb. 11, 2008

(86) PCT No.: PCT/US2008/053603
§ 371 (c)(1),
(2), (4) Date: Jan. 20, 2010

(87) PCT Pub. No.: WO2008/098248
PCT Pub. Date: Aug. 14, 2008

(65) Prior Publication Data
US 2010/0129808 A1 May 27, 2010

Related U.S. Application Data

(60) Provisional application No. 60/900,648, filed on Feb. 9, 2007, provisional application No. 60/956,205, filed on Aug. 16, 2007.

(51) Int. Cl.
*C07H 21/04* (2006.01)

(52) U.S. Cl.
USPC ........... 435/6.1; 435/7.1; 536/22.1; 536/23.1; 536/24.3

(58) Field of Classification Search
USPC ................ 435/6.1, 7.1, 23.1, 24.3; 536/22.1, 536/23.1, 24.3
See application file for complete search history.

(56) References Cited

U.S. PATENT DOCUMENTS

| | | | |
|---|---|---|---|
| 3,687,808 A | 8/1972 | Merigan et al. |
| 4,179,337 A | 12/1979 | Davis et al. |
| 4,289,872 A | 9/1981 | Denkewalter et al. |
| 4,301,144 A | 11/1981 | Iwashita et al. |
| 4,469,863 A | 9/1984 | Ts'o et al. |
| 4,476,301 A | 10/1984 | Imbach et al. |
| 4,489,055 A | 12/1984 | Couvreur et al. |
| 4,496,689 A | 1/1985 | Mitra |
| 4,587,044 A | 5/1986 | Miller et al. |
| 4,605,735 A | 8/1986 | Miyoshi et al. |
| 4,640,835 A | 2/1987 | Shimizu et al. |
| 4,667,025 A | 5/1987 | Miyoshi et al. |
| 4,670,417 A | 6/1987 | Iwasaki et al. |
| 4,762,779 A | 8/1988 | Snitman |
| 4,789,737 A | 12/1988 | Miyoshi et al. |
| 4,791,192 A | 12/1988 | Nakagawa et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,229,490 A | 7/1993 | Tam |
| 5,235,033 A | 8/1993 | Summerton et al. |
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,270,163 A | 12/1993 | Gold et al. |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |

(Continued)

FOREIGN PATENT DOCUMENTS

| | | | |
|---|---|---|---|
| EP | 1072679 A2 | 1/2001 |
| EP | 1674128 A1 | 6/2006 |

(Continued)

OTHER PUBLICATIONS

Raj et al. Stochastic mRNA synthesis in Mammalian cells. PLoS Biology 4(10) : e309 (Sep. 2006).*

(Continued)

*Primary Examiner* — Ethan C Whisenant
(74) *Attorney, Agent, or Firm* — Marshall, Gerstein & Borun LLP

(57) ABSTRACT

Methods describing the use of nanoparticles modified with binding moieties are provided.

9 Claims, 3 Drawing Sheets

(56) References Cited

U.S. PATENT DOCUMENTS

| | | |
|---|---|---|
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,457,272 A | 10/1995 | Hooykaas |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,472,881 A | 12/1995 | Beebe et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,547,842 A * | 8/1996 | Hogan et al. ............ 435/6.12 |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,637,459 A | 6/1997 | Burke et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,287,860 B1 | 9/2001 | Monia et al. |
| 6,361,944 B1 | 3/2002 | Mirkin et al. |
| 6,403,312 B1 | 6/2002 | Dahiyat et al. |
| 6,506,564 B1 | 1/2003 | Mirkin et al. |
| 6,544,776 B1 | 4/2003 | Gold et al. |
| 6,656,730 B1 | 12/2003 | Manoharan |
| 6,677,153 B2 | 1/2004 | Iversen |
| 6,709,825 B2 | 3/2004 | Mirkin et al. |
| 6,750,016 B2 | 6/2004 | Mirkin et al. |
| 6,767,702 B2 | 7/2004 | Mirkin et al. |
| 6,844,161 B2 | 1/2005 | Siani et al. |
| 6,991,900 B2 | 1/2006 | Shizuya |
| 7,098,320 B1 | 8/2006 | Mirkin et al. |
| 7,223,833 B1 | 5/2007 | Nielsen et al. |
| 7,238,472 B2 | 7/2007 | Mirkin et al. |
| 7,332,586 B2 | 2/2008 | Franzen et al. |
| 7,727,969 B2 | 6/2010 | Farokhzad et al. |
| 7,829,272 B2 * | 11/2010 | Tu et al. .................... 435/5 |
| 2002/0172953 A1 | 11/2002 | Mirkin et al. |
| 2003/0147966 A1 | 8/2003 | Franzen et al. |
| 2003/0181412 A1 | 9/2003 | Erikson |
| 2004/0219565 A1 | 11/2004 | Kauppinen et al. |
| 2004/0247680 A1 | 12/2004 | Farokhzad et al. |
| 2004/0248099 A1 | 12/2004 | Goppelt et al. |
| 2005/0059016 A1 | 3/2005 | Ecker et al. |
| 2005/0074753 A1 * | 4/2005 | Goldsborough ................ 435/5 |
| 2005/0096263 A1 | 5/2005 | Keay et al. |
| 2005/0136258 A1 | 6/2005 | Nie et al. |
| 2005/0197315 A1 | 9/2005 | Taira et al. |
| 2005/0214782 A1 | 9/2005 | Chen et al. |
| 2005/0244858 A1 | 11/2005 | Rossi et al. |
| 2006/0008907 A1 | 1/2006 | Friedman et al. |
| 2006/0019917 A1 | 1/2006 | Guerciolini et al. |
| 2006/0025363 A1 | 2/2006 | Breitenbach et al. |
| 2006/0035344 A1 | 2/2006 | Pachuk et al. |
| 2006/0105343 A1 | 5/2006 | Zetter et al. |
| 2006/0159921 A1 | 7/2006 | Murthy et al. |
| 2006/0183247 A1 | 8/2006 | Kim et al. |

| | | | |
|---|---|---|---|
| 2006/0188560 | A1 | 8/2006 | Cheresh et al. |
| 2006/0233712 | A1 | 10/2006 | Penades et al. |
| 2006/0252037 | A1 | 11/2006 | Kolesnick et al. |
| 2006/0275371 | A1 | 12/2006 | Dai et al. |
| 2007/0105139 | A1 | 5/2007 | Nishigaki et al. |
| 2008/0194463 | A1 | 8/2008 | Weller et al. |
| 2008/0213177 | A1 | 9/2008 | Rademacher et al. |
| 2008/0220072 | A1 | 9/2008 | Unger et al. |
| 2008/0279946 | A1 | 11/2008 | Hainfeld |
| 2008/0305106 | A1 | 12/2008 | Brennan et al. |
| 2008/0306016 | A1 | 12/2008 | Mirkin et al. |
| 2008/0317749 | A1 | 12/2008 | Kastelein et al. |
| 2008/0317768 | A1 | 12/2008 | Bianchi |
| 2009/0035576 | A1* | 2/2009 | Prasad et al. .......... 428/402 |
| 2009/0081244 | A1 | 3/2009 | Glenn et al. |
| 2009/0209434 | A1* | 8/2009 | Shafer ................. 506/9 |
| 2009/0209629 | A1 | 8/2009 | Mirkin et al. |
| 2009/0286853 | A1 | 11/2009 | Gryaznov et al. |
| 2010/0183634 | A1 | 7/2010 | Luo et al. |
| 2011/0172404 | A1 | 7/2011 | Luo et al. |
| 2011/0262976 | A1 | 10/2011 | Kandula et al. |

FOREIGN PATENT DOCUMENTS

| | | |
|---|---|---|
| WO | WO-89/02439 | 3/1989 |
| WO | WO-93/07883 | 4/1993 |
| WO | WO-93/21259 | 10/1993 |
| WO | WO-95/06731 | 3/1995 |
| WO | WO-95/11910 | 5/1995 |
| WO | WO-97/12896 A1 | 4/1997 |
| WO | WO-98/04740 A1 | 2/1998 |
| WO | WO-98/39352 A1 | 9/1998 |
| WO | WO-98/47343 A2 | 10/1998 |
| WO | WO-99/11655 A1 | 3/1999 |
| WO | WO-99/14226 A2 | 3/1999 |
| WO | WO-00/43045 | 7/2000 |
| WO | WO-01/00876 A1 | 1/2001 |
| WO | WO-01/49869 | 7/2001 |
| WO | WO-01/51665 A2 | 7/2001 |
| WO | WO-01/73123 A2 | 10/2001 |
| WO | WO-02/44321 A2 | 6/2002 |
| WO | WO-02/096262 A2 | 12/2002 |
| WO | WO-03/008539 A2 | 1/2003 |
| WO | WO-03/051278 | 6/2003 |
| WO | WO-2005/079462 A2 | 9/2005 |
| WO | WO-2005/116226 | 12/2005 |
| WO | WO-2006/012695 | 2/2006 |
| WO | WO-2006/045541 | 5/2006 |
| WO | WO-2006/138145 | 12/2006 |
| WO | WO-2008/141289 | 11/2008 |

OTHER PUBLICATIONS

Srivastava et al., Use of riboprobes for northern blotting analysis. Biotechniques 11(5) : Abstract Only (1991).*
Ahmadi et al., "Shape-controlled synthesis of colloidal platinum nanoparticles," *Science*, 272:1924-6 (1996).
Alivisatos et al., Organization of 'nanocrystal molecules' using DNA, *Nature*, 382:609-11 (1996).
Allara et al., "Spontaneously organized molecular assemblies. 1. Formation, dynamics and physical properties of n-Alkanoic acids adsorbed from solution on an oxidized aluminum surface," *Langmuir*,1: 45 (1985).
Allara et al., "The study of the gas-solid interaction of acetic acid with a cuprous oxide surface using reflection-absorption spectroscopy," *J. Colloid Interface Sci.*, 49: 410-421 (1974).
Altieri, Survivin, versatile modulation of cell division and apoptosis in cancer, *Oncogene*, 22:8581-9 (2003).
Altschul et al., "Basic local alignment search tool," *J. Mol. Biol.*, 215: 403-410 (1990).
Bratu et al., Visualizing the distribution and transport of mRNAs in living cells, *Proc. Natl. Acad. Sci. USA*, 100:13308-13 (2003).
Burwell, "Modified silica gels as adsorbents and catalysts," *Chemical Technology*, 4, 370-377 (1974).
Charreyre et al., "Fluorescence energy transfer study of the conformation of oligonucleotides covalently bound to polystyrene latex particles," *Langmuir*, 13:3103-3110 (1997).
Chrisey et al., Covalent attachment of synthetic DNA to self-assembled monolayer films, *Nucleic Acids Res.*, 24:3031-9 (1996).
Curtis et al., "A morphology-selective copper organosol," *Angew. Chem. Int. Ed. Engl.*, 27:1530-1533 (1988).
Demers et al., Combinatorial templates generated by dip-pen nanolithography for the formation of two-dimensional particle arrays, *Angew. Chem. Int. Ed.*, 40:3071-3 (2003).
DeMesmaeker et al., Backbone modifications in oligonucleotides and peptide nucleic acid systems, *Curr. Opin. Structural Biol.*, 5:343-55 (1995).
Devlin et al., Random peptide libraries: a source of specific protein binding molecules, *Science*, 249:404-6 (1990).
Dubertret et al., Single-mismatch detection using gold-quenched fluorescent oligonucleotides, *Nat. Biotechnol.*, 19:365-70 (2001).
Dulkeith et al., Gold nanoparticles quench fluorescence by phase induced radiative rate suppression, *Nano Lett.*, 5:585-9 (2005).
Elaissari et al., Effect of charge nature on the adsorption of single-stranded DNA fragments onto latex particles, *J. Colloid Interface Sci.*, 202:251-60 (1998).
Elghanian et al., Selective colorimetric detection of polynucleotides based on the distance-dependent optical properties of gold nanoparticles, *Science*, 277: 1078-81 (1997).
Eltekova et al., "Adsorption of aromatic compounds from solutions on titanium dioxide and silica", *Langmuir*, 3:951-957 (1987).
Englisch et al., Chemically modified oligonucleotides as probes and inhibitors, *Angew. Chem. Int. Ed. English*, 30:613-29 (1991).
Enustun et al., "Coagulation of colloidal gold", *J Am Chem Soc*, 85:3317-3328 (1963).
Fahy et al., Design and synthesis of polyacrylamide-based oligonucleotide supports for use in nucleic acid diagnostics, *Nucleic Acids Res.*, 21:1819-26 (1993).
Fattal et al., "Biodegradable polyalkylcyanoacrylate nanoparticles for the delivery of oligonucleotides,"*J. Control Release.*, 53:137-143 (1998).
Femino et al., Visualization of single RNA transcripts in situ, *Science*, 280:585-90 (1998).
Freier et al., The ups and downs of nucleic acid duplex stability: structure-stability studies on chemically-modified DNA:RNA duplexes, *Nucleic Acids Res.*, 25:4429-43 (1997).
Frens, Controlled nucleation for the regulation of the particle size in monodisperse gold suspensions, *Nature Physical Science*, 241:20-2 (1973).
Grabar et al., "Preparation and characterization of Au colloid monolayers", *Anal Chem*, 67 :735-743 (1995).
Hayashi, "Ultrafine particles", *Physics Today*, pp. 44-60 (Dec. 1987).
Hayashi, "Ultrafine particles", *Vac. Sci. Technol.*, A5(4):1375-84 (1987).
Hayat (ed.), *Colloidal Gold: Principles, Methods, and Applications* (Academic Press, San Diego, 1991).
Henglein et al., "Adsorption spectrum and some chemical reactions of colloidal platinum in aqueous solution", *J Phys Chem*, 99: 14129-36 (1995).
Hickman et al., "Combining spontaneous molecular assembly with microfabrication to pattern surfaces: selective binding of isonitriles to platinum microwires and characterization by electrochemistry and surface spectroscopy", *J. Am. Chem. Soc.*, 111: 7271-7272 (1989).
Hubbard, "Electrochemistry of well-defined surfaces", *Acc. Chem. Res.*, 13:177-184 (1980).
Iler, *The Chemistry of Silica*, Chapter 6, New York: Wiley (1979).
International Preliminary Report on Patentability for or corresponding International Application No. PCT/US2008/053603, dated Aug. 11, 2009.
International Search Report and Written Opinion for corresponding International Application No. PCT/US2008/053603, dated Sep. 15, 2008.
Kloosterman et al., In situ detection of miRNAs in animal embryos using LNA-modified oligonucleotide probes, *Nat. Methods*, 3:27-9 (2006).
Kolarova et al., Preparation of magnetic oligo (dT) particles, *Biotechniques*, 20:196-8 (1996).
Kukowska-Latallo et al., Efficient transfer of genetic material into mammalian cells using Starburst polyamidoamine dendrimers, *Proc. Natl. Acad. Sci. USA*, 93:4897-902 (1996).

Lee et al., "Adsorption of ordered zirconium phosphonate multilayer films on silicon and gold surfaces", *J. Phys. Chem.*, 92 : 2597-601 (1988).

Liu et al., New poly(d-glucaramidoamine)s induce DNA nanoparticle formation and efficient gene delivery into mammalian cells, *J. Am. Chem. Soc.* 126:7422-7423 (2004).

Love et al., Self-assembled monolayers of thiolates on metals as a form of nanotechnology, *Chem. Rev.* 105:1103-69 (2005).

Lytton-Jean et al., A thermodynamic investigation into the binding properties of DNA functionalized gold nanoparticle probes and molecular fluorophore probes, *J. Am. Chem Soc.*, 127: 12754-5 (2005).

Maoz et al., "Penetration-controlled reactions in organized monolayer assemblies. 1. Aqueous permanganate interaction with monolayer and multilayer films of long-chain surfactants", *Langmuir*, 3:1034-1044 (1987).

Maoz et al., "Penetration-controlled reactions in organized monolayer assemblies. 2. Aqueous permanganate interaction with self-assembling monolayers of long-chain surfactants," *Langmuir*, 3:1045-1051 (1987).

Marinakos et al., "Gold nanoparticles as templates for the synthesis of hollow nanometer-sized conductive polymer capsules", *Ad. Mater*, 11:34-37 (1999).

Marinakos et al., "Template synthesis of one-dimensional Au, Au—poly(pyrrole), and poly(pyrrole) nanoparticle arrays", *Chem Mater*, 10:1214-19 (1998).

Martin et al., 38. Fin neuer zugang zu 2'-O-alkylribonucleosiden und eigenschaften deren oligonucleotide, *Helv. Chim. Acta*, 78:486-504 (1995) [English abstract only.].

Massart, "Preparation of aqueous magnetic liquids in alkaline and acidic media", *IEEE Transactions on Magnetics*, 17:1247-8 (1981).

Matsuura et al., Construction and characterization of protein libraries composed of secondary structure modules, *Protein Sci.*, 11:2631-43 (2002).

Matteucci et al., "Synthesis of deoxyoligonucleotides on a polymer support", *J Am Chem Soc*, 103, 3185-3191 (1981).

Maxwell et al., Self-assembled nanoparticle probes for recognition and detection of biomolecules, *J. Am. Chem. Soc.*, 124:9606-12 (2002).

Mirkin et al., A DNA-based method for rationally assembling nanoparticles into macroscopic materials, *Nature*, 382: 607 (1996).

*MRS Bulletin, Fine Particles Pt. II*, pp. 16-47 (Jan. 1990).

Mucic et al., "Synthesis and characterization of DNA with ferrocenyl groups attached to their 5-termini: electrochemical characterization of a redox-active nucleotide monolayer", *Chem Commun*, 555-557 (1996).

Nam et al., Nanoparticle-based bio-bar codes for the ultrasensitive detection of proteins, *Science*, 301: 1884-6 (2003).

Nielsen et al., Sequence-selective recognition of DNA by strand displacement with a thymine-substituted polyamide, *Science*, 254:1497-500 (1991).

Nitin et al., Peptide-linked molecular beacons for efficient delivery and rapid mRNA detection in living cells, *Nucleic Acids Res.*, 32:e58 (2004).

Nuzzo et al., "Spontaneously organized molecular assemblies. 3. Preparation and properties of solution adsorbed monolayers of organic disulfides on gold surfaces," *J Am Chem Soc*, 109:2358-2368 (1987).

Ohuchi et al., In vitro method for the generation of protein libraries using PCR amplification of a single DNA molecule and coupled transcription/translation, *Nucleic Acids Res.*, 26:4339-46 (1998).

Opalinska et al., Nucleic-acid therapeutics: basic principles and recent applications, *Nat. Rev. Drug Discov.*, 1:503-14 (2002).

Peng et al., Real-time detection of gene expression in cancer cells using molecular beacon imaging: new strategies for cancer research, *Cancer Res.*, 65:1909-17 (2005).

Penn et al., Nanoparticles for bioanalysis, *Curr. Opin. Chem. Biol.*, 7:609-15 (2003).

Perlette et al., Real-time monitoring of intracellular mRNA hybridization inside single living cells, *Anal. Chem.*, 73:5544-50 (2001).

Rizzo et al., Chimeric RNA-DNA molecular beacon assay for ribonuclease H activity, *Mol. Cell Probes*, 16:277-83 (2002).

Rosi et al., Oligonucleotide-modified gold nanoparticles for intracellular gene regulation, *Science*, 312:1027-30 (2006).

Sandhu et al., Gold nanoparticle-mediated transfection of mammalian cells, *Bioconjug. Chem.*, 13:3-6 (2002).

Sanghvi et al., Heterocyclic base modifications in nucleic acids and their applications in antisense oligonucleotides, Chapter 15 IN: Crooke et al. (eds.), *Antisense Research and Applications*, Boca Raton: CRC Press (1993).

Santangelo et al., Dual FRET molecular beacons for mRNA detection in living cells, *Nucleic Acids Res.*, 32:e57 (2004).

Santangelo et al., Nanostructured probes for RNA detection in living cells, *Ann. Biomed. Eng.*, 34:39-50 (2006).

Seferos et al., Locked nucleic acid-nanoparticle conjugates, *Chembiochem.*, 8:1230-2 (2007).

Seferos et al., Nano-flares: probes for transfection and mRNA detection in living cells, *J. Am. Chem. Soc.*, 129:15477-9 (2007).

Sokol et al., Real time detection of DNA.RNA hybridization in living cells, *Proc. Natl. Acad. Sci. USA*, 95:11538-43 (1998).

Soriaga et al., "Determination of the orientation of aromatic molecules adsorbed on platinum electrodes. The effect of solute concentration", *J Am Chem Soc*, 104:3937-45 (1982).

Timmons et al., "Investigation of fatty acid monolayers on metals by contact potential measurements", *J Phys Chem*, 69:984-990 (1965).

Tkachenko et al., Multifunctional gold nanoparticle-peptide complexes for nuclear targeting, J. Am. Chem. Soc., 125:4700-1 (2003).

Tondelli, et al., "Highly efficient cellular uptake of c-myb antisense oligonucleotides through specifically designed polymeric nanospheres," *Nucleic Acids Res..*, 26:5425-5431 (1998).

Tyagi et al., Molecular beacons: probes that fluoresce upon hybridization, *Nat. Biotechnol.*, 14:303-8 (1996).

Wasserman et al., "Structure and reactivity of alkylsiloxane monolayers formed by reaction of alkyltrichlorosilanes on silicon substrates", *Langmuir*, 5:1074-1087 (1989).

Whitesides, *Proceedings of the Robert A. Welch Foundation 39th Conference on Chemical Research Nanophase Chemistry*, Houston, Tex., pp. 109-121 (1995).

Wolf et al., Rapid hybridization kinetics of DNA attached to submicron latex particles, *Nucleic Acids Res.*, 15:2911-26 (1987).

Zabner et al., Cellular and molecular barriers to gene transfer by a cationic lipid, *J. Biol. Chem.*, 270:18997-9007 (1995).

Zhang et al., PowerBlast: A new network BLAST application for interactive or automated sequence analysis and annotation, *Genome*, 7:649-56 (1997).

Zhang et al., Single-quantum-dot-based DNA sensor, *Nat. Mater.*, 4:826-31 (2005).

Amirkhanov et al., Design of (Gd-DO3A)n-polydiamidopropanoyl-peptide nucleic acid-D(Cys-Ser-Lys-Cys) magnetic resonance contrast agents. *Biopolymers*, 89(12): 1061-76 (2008).

Aynie, et al., Spongelike alginate nanoparticles as a new potential system for the delivery of antisense oligonucleotides. Antisense Nucl. Acid Drug Dev., 9: 301-12 (1999).

Bahnemann, Photochemical Conversion and Storage of Solar Energy, Pelizetti and Schiavello (Eds.) pp. 251-276 (1991).

Baker et al., Dendrimer-mediated cell transfection in vitro. Meth. Molec. Biol., 245: 67-81 (2004).

Bath et al., DNA nanomachines, Nat. Nanotechnol., 2: 275-84 (2007).

Baudhuim, Photochemical conversion and storage of solar energy. Kluwer Academic Publishers. 251-76 (1990).

Baudhuin et al., Molecular interactions between colloidal gold, proteins, and living cells. Chapter 1: 1-17 (1989).

Berton, et al., Highly loaded nanoparticulate carrier using an hydrophobic antisense oligonucleotide complex, Eur. J. Pharma. Sci., 9: 163-70 (1999).

Besch et al., Characterization and quantification of triple helix formation in chromosomal DNA. J. Mol. Biol., 341: 979-89 (2004).

Bharali et al., Organically modified silica nanoparticles: a nonviral vector for in vivo gene delivery and expression in the brain. Proc. Natl. Acad. Sci. USA, 102(32): 11539-44 (2005).

Bielinska et al., DNA complexing with polyamidoamine dendrimers: implications for transfection. Bioconjug Chem., 10(5): 843-50 (1999).

Birck et al., Mutation and allelic loss of the PTEN/MMAC1 gene in primary and metastatic melanoma biopsies, J. Invest. Dermatol., 114: 277-80 (2000).

Bramhill, Bacterial cell division, *Annu. Rev. Cell Dev. Biol.*, 13: 395-424 (1997).

Brus, Quantum crystallites and nonlinear optics. Appl. Phys. A. 53(6): 465-74 (1991).

Capaccioli et al., Cationic lipids improve antisense oligonucleotide uptake and prevent degradation in cultured cells and inhuman serum, Biochem. Biophys. Res. Commun., 197(2): 818-25 (1993).

Castoldi et al., A sensitive array for microRNA expression profiling (miChip) based on locked nucleic acids (LNA), RNA. 12: 913-20 (2006).

Chavany et al., Polyalkylcyanoacrylate nanoparticles as polymeric carriers for antisense oligonucleotides, Pharma. Res., 9(4): 441-9 (1992).

Chavany, et al., Adsorption of oligonucleotides onto polyisohexylcyanoacrylate nanoparticles protects them against nucleases and increases their cellular uptake. Pharma. Res., 11(9): 1370-8 (1994).

Chen et al., Kinetics and thermodynamics of DNA hybridization on gold nanoparticles, Nucl. Acids Res., 37: 3756-65 (2009).

Cheung et al., Akt3 and mutant V600E B-Raf cooperate to promote early melanoma development, Cancer Res., 68:3429-39 (2008).

Chithrani et al., Elucidating the mechanism of cellular uptake and removal of protein-coated gold nanoparticles of different sizes and shapes. Nano Lett., 7: 1542-50 (2007).

Chithrani, et al., Determining the size and shape dependence of gold nanoparticle uptake into mammalian cells, Nano Lett., 6(4): 662-8 (2006).

Cload et al., Polyether tethered oligonucleotide probes. J. Am. Chem. Soc., 113(16): 6324-6 (1991).

Cook, Medicinal chemistry of antisense oligonucleotides—future opportunities. Anticancer Drug Des., 6(6):585-607 (1991).

Crawford et al., A novel B-RAF inhibitor blocks interleukin-8 (IL-8) synthesis in human melanoma xenografts, revealing IL-8 as a potential pharmacodynamic biomarker, Mol. Cancer Ther., 7: 492-9 (2008).

Crawford et al., Peptide aptamers: Tools for biology and drug discovery. 2(1): 72-9 (2003).

Daniel et al., Gold nanoparticles: assembly, supramolecular chemistry, quantum-size-related properties, and applications toward biology, catalysis, and nanotechnology. Chem Rev., 104(1): 293-346 (2004).

Dankort et al., A new mouse model to explore the initiation, progression, and therapy of BRAFV600E-induced lung tumors, Genes Dev., 21: 379-84 (2007).

Dankort et al., Braf(V600E) cooperates with Pten loss to induce metastatic melanoma, Nat Genet., 41: 544-52 (2009).

Davies et al., A novel AKT3 mutation in melanoma tumours and cell lines, Br. J. Cancer, 99: 1265-8 (2008).

DeMesmaeker et al., Antisense oligonucleotides. Acc. Chem. Res., 28(9): 366-74 (1995).

Dhar et al., Polyvalent oligonucleotide gold nanoparticle conjugates as delivery vehicles for platinum(IV) warheads. *J. Am. Chem. Soc.*, 131(41): 14652-3 (2009).

Dhar et al., Targeted single wall carbon nanotube mediated Pt(IV) prodrug delivery using folate as a homing device. *J. Am. Chem. Soc.*, 130(34): 11467-76 (2008).

Dhomen et al., BRAF signaling and targeted therapies in melanoma, Hematol. Oncol. Clin. North Am., 23: 529-45, ix (2009).

Donachie, The cell cycle of *Escherichia coli*., *Annu. Rev. Microbiol.*, 47: 199-230 (1993).

Dreyfus et al., Simple quantitative model for the reversible associate of DNA coated colloids, Phys. Rev. Lett., 102: 048301 (2009).

Durand et al., Circular dichroism studies of an oligodeoxyribonucleotide containing a hairpin loop made of a hexaethylene glycol chain: conformation and stability. Nucl. Acids Res. , 18(21): 6353-9 (1990).

Eckstein (Ed.), Oligonucleotides and analogues, 1st Ed., Oxford University Press, New York (1991).

Endres et al., DNA-TiO2 nanoconjugates labeled with magnetic resonance contract agents. *J. Am. Chem. Soc.* 129(51): 15760-1 (2007).

Faulds et al., Evaluation of surface-enhanced resonance Raman scattering for quantitative DNA analysis. Anal. Chem., 76: 412-7 (2004).

Ferentz et al., Disulfide-crosslinked oligonucleotides. J. Am. Chem. Soc., 113(10): 4000-2 (1991).

Flandroy et al., (D, L)Polyactide microspheres as embolic agent. *Neuroradiology*, 32: 311-5 (1990).

Gao et al., Secondary structure effects on DNA hybridization kinetics: a solution versus surface comparison. Nucl. Acids Res., 34: 3370-7 (2006).

Gerdes et al., Experimental determination and system level analysis of essential genes in *Escherichia coli* MG1655. *J. Bacteriol.*, 185: 5673-84 (2003).

Gestwicki et al., Influencing receptor-ligand binding mechanisms with multivalent ligand architecture. J. Am. Chem. Soc., 124: 14922-33 (2002).

Gidwani et al., Hybridization kinetics of double-stranded DNA probes for rapid molecular analysis. Analyst, 134: 1675-81 (2009).

Giljohann et al., Gene regulation with polyvalent siRNA-nanoparticle conjugates. J. Am. Chem. Soc., 131:2072-3 (2009).

Giljohann et al., Oligonucleotide loading determines cellular uptake of DNA-modified gold nanoparticles. Nano Lett., 7(12): 3818-21 (2007).

Goel et al., Melanocytic nevus-like hyperplasia and melanoma in transgenic BRAFV600E mice. Oncogene, 28: 2289-98 (2009).

Guo et al., Cell-SELEX: Novel perspectives of aptamer-based therapeutics, Int. J. Mol. Sci., 9: 668-78 (2008).

Hale et al., Recruitment of ZipA to the septal ring of *Escherichia coli* is dependent on FtsZ and independent of FtsA. *J. Bacteriol.*, 181: 167-76 (1999).

Hamilton et al., A species of small antisense RNA in post-transcriptional gene silencing in plants. Science, 286: 950-2 (1999).

Hammond et al., An RNA-directed nuclease mediates post-transcriptional gene silencing in *Drosophilia* cells. Nature, 404: 293-6 (2000).

He et al., Colloidal Au-enhanced surface plasmon resonance for ultrasensitive detection of DNA hybridization. J. Am. Chem. Soc., 122(38): 9071-7 (2000).

Henglein, Mechanism of reactions on colloidal microelectrodes and size quantization effects. Top. Curr. Chem., 143: 113-80 (1998).

Henglein, Small-particle research: physicochemical properties of extremely small colloidal metal and semiconductor particles. Chem. Rev., 89(8): 1861-73 (1989).

Hurst et al., Maximizing DNA loading on a range of gold nanoparticle sizes. Anal. Chem., 78: 8313 (2006).

Hussain et al., A novel anionic dendrimer for improved cellular delivery of antisense oligonucleotides. J. Controlled Rel., 99: 139-55 (2004).

Introducing Antisense Oligonucleotides into Cells, Innovation & Precision in Nucleic Acid Synthesis, Integrated DNA Technologies (2005).

Jackson et al., *Escherichia coli* O157:H7 diarrhoea associated with well water and infected cattle on an Ontario farm, *Epidemiol. Infect.*, 120:17-20 (1998).

Jaschke et al., Automated incorporation of polyethylene glycol in synthetic oligonucleotides. Tetrahedron Lett., 34: 301-4 (1993).

Jason et al., Toxicology of antisense therapeutics. Toxicol. Appl. Pharmacol., 201(1): 66-83 (2004).

Jen et al., A nonviral transfection approach in vitro: the design of a gold nanoparticle vector joint with microelectromechanical systems. Langmuir, 20(4): 1369-74 (2004).

Jeong et al., Novel intracellular delivery system of antisense oligonucleotide by self-assembled hybrid micelles composed of DNA/PEG conjugate and cationic fusogenic peptide. Bioconjugate Chem., 14: 473-9 (2003).

Jin et al., What controls the melting properties of DNA-linked gold nanoparticle assemblies? J. Am. Chem. Soc., 125: 1643 (2003).

Katz et al., Integrated nanoparticle-biomolecule hybrid systems: synthesis, properties, and applications, Angew. Chem. Int. Ed., 43: 6042-108 (2004).

Katz, The reversible reaction of sodium thymonucleate and mercuric chloride, *J. Am. Chem. Soc.*, 74: 2238-45 (1952).

Kopylov et al., Combinatorial chemistry of nucleic acids: SELEX, Mol. Biol., 34: 940-54 (2000).

Kosturko et al., The crystal and molecular structure of a 2:1 complex of 1-methylthymine-mercury(II), Biochem., 13: 3949-52 (1974).

Kroschwitz (Ed.), The Concise Encyclopedia of Polymer Science and Engineering, pp. 858-859, John Wiley & Sons (1990).

Lannutti et al., Human angiostatin inhibits murine hemangioendothelioma tumor growth in vivo, Cancer Res., 57: 5277-80 (1997).

Lebedeva et al., Antisense oligonucleotides: Promise and reality. Annu. Rev. Pharmacol. Toxicol., 41: 403-19 (2001).

Lemaigre et al., Transcriptional control of genes that regulate glycolysis and gluconeogenesis in adult liver, Biochem. J., 303: 1-14 (1994).

Leslie et al., A new tool for oligonucleotides import into cells. Clin. Chem., 55: 609-10 (2009).

Leunissen et al., Switchable self-protected attractions in DNA-functionalized colloids. Nat. Mater., 8: 590-95 (2009).

Lin et al., Effector/memory but not naive regulatory T cells are responsible for the loss of concomitant tumor immunity. J. Immunol., 182: 6095-104 (2009).

Lin et al., Modeling genomic diversity and tumor dependency in malignant melanoma. Cancer Res., 68: 664-73 (2003).

Lipshutz et al., High density synthetic oligonucleotide arrays. Nanotechnology, 14: R15-27 (2003).

Liu et al., Accelerated color change of gold nanoparticles assembled by DNAzymes for simple and fast colorimetric Pb2+ detection. J. Am. Chem. Soc., 126: 12298-305 (2004).

Liu et al., ARDB—Antibiotic Resistance Genes Database. Nucl. Acids Res., 37: D443-7 (2009).

Liu et al., Argonaute2 is the catalytic engine of mammalian RNAi. Science, 305(5689): 1437-41 (2004).

Liu et al., De-N-acetyl GM3 promotes melanoma cell migration and invasion through urokinase plasminogen activator receptor signaling-dependent MMP-2 activation. Cancer Res., 69: 8662-9 (2009).

Liu et al., Synthesis, stability, and cellular internalization of gold nanoparticles containing mixed peptide-poly(ethylene glycol) monolayers. Anal. Chem., 79: 2221-9 (2007).

Loeken, Effects of mutation of the CREB binding site of the somatostatin promoter on cyclic AMP responsiveness in CV-1 cells. Gene Expr., 3: 253-64 (1993).

Lutkenhaus et al., Bacterial cell division and the Z ring. Annu. Rev. Biochem., 66: 93-116 (1997).

Ma et al., Design and synthesis of RNA miniduplexes via a synthetic linker approach. 2. Generation of covalently closed, double-stranded cyclic HIV-1 TAR RNA analogs with high Tat-binding affinity. Nucl. Acids Res., 21: 2585-9 (1993).

Ma et al., Design and synthesis of RNA miniduplexes via a synthetic linker approach. Biochemistry, 32(7): 1751-8 (1993).

Martinez et al., Locked nucleic acid based beacons for surface interaction studies and biosensor development. Anal. Chem., 81: 3448-54 (2009).

Maruyama, et al., Nanoparticle DNA carrier with poly(L-lysine) grafted polysaccharide copolymer and poly(D,L-lactic acid). Bioconjugate Chem., 8: 735-742 (1997).

Maye et al., A simple method for kinetic control of DNA-induced nanoparticle assembly. J. Am. Chem. Soc., 128: 14020-1 (2006).

Mayer (ed.), Nucleic Acid and Peptide Aptamers: Methods and Protocols (Humana Press, 2009).

McCurdy et al., Deoxyligonucleotides with inverted polarity: Synthesis and use in triple-helix formation. Nucleosides & Nucleotides, 10: 287-90 (1991).

McGehee et al., Differentiation-specific element: a cis-acting developmental switch required for the sustained transcriptional expression of the angiotensinogen gene during hormonal-induced differentiation of 3T3-L1 fibroblasts to adipocytes. Mol. Endocrinol., 7: 551-60 (1993).

McKenzie et al., Sequence-specific DNA detection using high-affinity LNA-functionalized gold nanoparticles. Small, 3(11): 1866-8 (2007).

McManus et al., Gene silencing in mammals by small interfering RNAs. Nat. Rev. Genet, 3(10): 737-47 (2002).

Miller et al., Antisense oligonucleotides: Strategies for delivery. PSTT, 1(9): 377-86 (1998).

Milne et al., An approach to gene-specific transcription inhibition using oligonucleotides complementary to the template strand of the open complex. Proc. Natl. Acad. Sci. USA, 97(7): 3136-41 (2000).

Myers et al., A cyclopentane conformational restraint for a peptide nucleic acid: design, asymmetric synthesis, and improved binding affinity to DNA and RNA. Org Lett., 5(15): 2695-8 (2003).

Nykypanchuk et al., DNA-guided crystallization of colloidal nanoparticles. Nature, 451: 549-52 (2008).

Olshaysky et al., Organometallic synthesis of gallium-arsenide crystallites, exhibiting quantum confinement. J. Am. Chem. Soc., 112(25): 9438-9 (1990).

O'Meara et al., Capture of single-stranded DNA assisted by oligonucleotide modules. Anal. Biochem., 255: 195-203 (1998).

Ono et al., DNA triplex formation of oligonucleotide analogues consisting of linker groups and octamer segments that have opposite sugar-phosphate backbone polarities. Biochemistry, 30(41): 9914-2 (1991).

O'Reilly et al., Identification of an activating transcription factor (ATF) binding site in the human transforming growth factor-beta 2 promoter. J. Biol. Chem., 267: 19938-43 (1992).

Ow Sullivan et al., Development of a novel gene delivery scaffold utilizing colloidal gold-polyethylenimine conjugates for DNA condensation. Gene Ther., 10(22): 1882-90 (2003).

Parak et al., Biological applications of colloidal nanocrystals, Nanotechnol., 14: R15-27 (2003).

Park et al., Array-based electrical detection of DNA with nanoparticle probes. Science, 295: 1503-6 (2002).

Park et al., DNA-programmable nanoparticle cystrallization. Nature, 451: 553-6 (2008).

Parrish et al., Functional anatomy of a dsRNA trigger: Differential requirement for the two trigger strands in RNA interference. Mol. Cell, 6: 1077-87 (2000).

Patel et al., Peptide antisense nanoparticles. Proc. Natl. Acad. Sci. USA, 105: 17222-6 (2008).

Patil et al., DNA-based therapeutics and DNA delivery systems: a comprehensive review. AAPS J., 7(1): E61-77 (2005).

Paunecku et al., Godolinium-conjugated Ti02-DNA oligonucleotide nanocanjugates show prolonged intracellular retention period and Tl-weighted contract enhancement in magnetic resonance images. Nanomedicine, 4(3): 201-7 (2008).

Pon, Solid-phase supports for oligonucleotide synthesis. Meth. Molec. Biol., 20: 465-96 (1993).

Prausnitz et al., Transdermal drug delivery, Nat. Biotechnol., 26: 1261-8 (2008).

Prigodich et al., Nano-flares for mRNA regulation and detection. ACS Nano, 3: 2147-52 (2009).

Prime et al., Self-assembled organic monolayers; Model systems for studing adsorption of proteins at surfaces. Science, 252: 1164-7 (1991).

Riccelli et al., Hybridization of single-stranded DNA targets to immobilized complementary DNA probes: comparison of hairpin versus linear capture probes. Nucl. Acids Res., 29: 996-1004 (2001).

Richardson et al., Tethered oligonucleotide probes. A strategy for the recognition of structured RNA. J. Am. Chem. Soc., 113(13): 5109-11 (1991).

Rihova et al., Receptor-mediated targeted drug or toxin delivery. Adv. Drug Deliv. Rev., 29(3): 273-89 (1998).

Rosi et al., Nanostructures in biodiagnostics. Chem Rev., 105(4): 1547-62 (2005).

Rosi et al., Oligonucleotide-modified gold nanoparticles for intracellular gene regulation. Science, 2312(5776): 1027-30 (2006).

Sambrook et al., Molecular Cloning: A Laboratory Manual, 2nd Edition, Table of Contents, pp. v-xxxii (1989).

Schifferlers et al., Cancer siRNA therapy by tumor selective delivery with ligand-targeted sterically stabilized nanoparticle. Nucl. Acid Res., 32(19): e149 (2004).

Schmid, G. (ed.) Clusters and Colloids (VCH, Weinheim, 1994).

Seela et al., Oligodeoxyribonucleotides containing 1,3-propanediol as nucleoside substitute. Nucl. Acids Res., 15(7): 3113-29 (1987).

Seelig et al., Catalyzed relaxation of a metastable DNA fuel. J. Am. Chem. Soc., 128: 12211-20 (2006).

Seferos et al., Polyvalent DNA nanoparticle conjugates stabilize nucleic acids. Nano Lett., 9: 308-11 (2009).

Sharma et al., Mutant V599EB-Raf regulates growth and vascular development of malignant melanoma tumors. Cancer Res., 65: 2412-21 (2005).

Sharma et al., Targeting Akt3 signaling in malignant melanoma using isoselenocyanates. Clin. Cancer Res., 15:.1674-85 (2009).

Sharma et al., Targeting mitogen-activated protein kinase/extracellular signal-regulated kinase kinase in the mutant (V600E) B-Raf signaling cascade effectively inhibits melanoma lung metastases. Cancer Res., 66: 8200-9 (2006).

Sharp et al., RNA interference—2001. Genes Dev., 15: 485-90 (2001).

Simmel et al., DNA nanodevices. Small, 1: 284-99 (2005).

Stahl et al., Deregulated Akt3 activity promotes development of malignant melanoma, Cancer Res., 64: 7002-10 (2004).

Stephenson et al., Inhibition of Rous sarcoma viral RNA translation by a specific oligodeoxyribonucleotide. Proc. Natl. Acad. Sci. USA, 75(1): 285-8 (1978).

Stoermer et al., Distance-dependent emission from dye-labeled oligonucleotides on striped Au/Ag nanowires: effect of secondary structure and hybridization efficiency. J. Am. Chem. Soc., 128: 13243-54 (2006).

Stoeva et al., Multiplexed detection of protein cancer markers with biobarcoded nanoparticle probes. J. Am. Chem. Soc., 128: 8378-9 (2006).

Storhoff et al., What controls the optical properties of DNA-linked gold nanoparticle assemblies? J. Am. Chem. Soc., 122: 4640-50 (2000).

Sun et al., Ganglioside loss promotes survival primarily by activating integrin-linked kinase/Akt without phosphoinositide 3-OH kinase signaling. J. Invest. Dermatol., 119: 107-17 (2002).

Sundaram et al., Particle-mediated delivery of recombinant expression vectors to rabbit skin induces high-titered polyclonal antisera (and circumvents purification of a protein immunogen). Nucl. Acids Res., 24(7): 1375-7 (1996).

Thomas et al., Conjugation to gold nanoparticles enhances polyethylenimine's transfer of plasmid DNA into mammalian cells. Proc. Natl. Acad. Sci. USA, 100(16): 9138-43 (2003).

Thomas et al., The interaction of HgC12 with sodium thymonucleate. J. Am. Chem. Soc., 76: 6032-4 (1954).

Thompkins et al., The study of the gas-solid interaction of acetic acid with a cuprous oxide surface using reflection-absorption spectroscopy. J. Colloid Interface Sci., 49: 410-21 (1974).

Thurn et al., Labeling Ti02 nanoparticles with dyes for optical fluorescence microscopy and determination of Ti02—DNA nanoconjugate stability. Small, 5(11): 1318-25 (2009).

Tkachenko et al., Cellular trajectories of peptide-modified gold particle complexes: comparison of nuclear localization signals and peptide transduction domains. Bioconjugate Chem., 15(3): 482-90 (2004).

Treisman, The SRE: a growth factor responsive transcriptional regulator. Semin. Cancer Biol., 1: 47-58 (1990).

Tsao et al., Genetic interaction between NRAS and BRAF mutations and PTEN/MMAC1 inactivation in melanoma. J. Invest. Dermatol., 122: 337-41 (2004).

Tuerk et al., Systematic evolution of ligands by exponential enrichment: RNA ligands to bacteriophage T4 DNA polymerase. Science, 249: 505-10 (1990).

Turberfield et al., DNA fuel for free-running nanomachines. Phys. Rev. Lett., 90: 118102 (2003).

Uchida et al., GaAs nanocrystals prepared in quinoline. J. Phys. Chem. 95(14): 5382-4 (1991).

Vasiliskov et al., Parallel multiplex thermodynamic analysis of coaxial base stacking in DNA duplexes by oligodeoxyribonucleotide microchips. Nucl. Acids Res., 29: 2303-13 (2001).

Wagner et al., Gene inhibition using antisense oligodeoxynucleotides. Nature, 372: 333-5 (1994).

Wang et al., Ganglioside GM3 inhibits matrix metalloproteinase-9 activation and disrupts its association with integrin, J. Biol. Chem., 278: 25591-9 (2003).

Wang et al., Ganglioside GM3 promotes carcinoma cell proliferation via urokinase plasminogen activator-induced extracellular signal-regulated kinase-independent p70S6 kinase signaling, J. Invest. Dermatol., 126: 2687-96 (2006).

Wang et al., Inhibition of integrin-linked kinase/protein kinase B/Akt signaling: mechanism for ganglioside-induced apoptosis. J. Biol. Chem., 276: 44504-11 (2001).

Wang et al., Locked nucleic acid molecular beacons. J. Am. Chem. Soc., 127: 15664-5 (2005).

Wang et al., Molecular engineering of DNA: molecular beacons. Angew. Chem., Int. Ed., 48: 856-70 (2009).

Wang et al., Nanometer-sized semiconductor clusters: materials synthesis, quantum size effects, and photophysical properties. J. Phys. Chem., 95(2): 525-32 (1991).

Wang et al., Nanoparticles for multiplex diagnostics and imaging. Nanomedicine (Lond.), 1: 413-26 (2006).

Wang et al., Speeding up a single-molecule DNA device with a simple catalyst. Phys. Rev. E Stat. Nonlin. Soft Matter. Phys., 72: 051918 (2005).

Watson et al. (Eds.), *Molecular Biology of the Gene*, 4th ed., The Benjamin/Cummings Publishing Company Inc. (1987).

Wei et al., A study of the relationships between oligonucleotide properties and hybridization signal intensities from NimbleGen microarray datasets. Nucl. Acids Res., 36: 2926-38 (2008).

Wellbrock et al., V599EB-RAF is an oncogene in melanocytes. Cancer Res., 64: 2338-42 (2004).

Weller, Colloidal Semiconductor Q-particles: Chemistry in the transition region between solid state and molecules. Angew. Chem. Int. Ed. Engl., 32(1): 41-53 (1993).

Xu et al., Thermodynamics of DNA hybridization on gold nanoparticles. J. Am. Chem. Soc., 127(38): 13227-31 (2005).

Yamane et al., On the complexing of desoxyribonucleic acid (DNA) by mercuric ion. *J. Am. Chem. Soc.*, 83: 2599-607 (1961).

Yan et al., Aptamers and aptamer targeted delivery. RNA Biol., 6: 316-20 (2009).

Yang et al., Evidence that processed small dsRNAs may mediate sequence-specific mRNA degradation during RNAi in *Drosophila* embryos. Curr. Biol., 10: 1191-200 (2000).

Ye et al., Characterization of a silencer regulatory element in the human interferon-gamma promoter. *J. Biol. Chem.*, 269: 25728-34 (1994).

Yin Win et al., Effects of particle size and surface coating on cellular uptake of polymeric nonparticles for oral delivery of anticancer drugs. Biomaterials, 26: 2713-22 (2005).

You et al., Detection and identification of proteins using nanoparticle-fluorescent polymer 'chemical nose' sensors. Nat. Nanotechnol., 2: 318-23 (2007).

You et al., Engineering the nanoparticle-biomacromolecule interface. Soft Matter, 2: 190-204 (2006).

Zamecnik et al., Inhibition of *Rous sarcoma* virus replication and cell transformation by a specific oligodeoxynucleotide. Proc. Natl. Acad. Scci. USA, 75(1): 280-4 (1978).

Zamore et al., RNAi: double-stranded RNA directs the ATP-dependent cleavage of mRNA at 21 to 23 nucleotide intervals. Cell, 101: 25-33 (2000).

Zhang et al., An extremely stable and orthogonal DNA base pair with a simplifed three-carbon backbone. *J. Am. Chem. Soc.*, 127: 74-5 (2005).

Zhang et al., Control of DNA strand displacement kinetics using toehold exchange. J. Am. Chem. Soc., 131: 17303-14 (2009).

Zheng et al., Aptamer nano-flares for molecular detection in living cells. Nano Lett., 9: 3258-61 (2009).

Zimmer, Antisense oligonucleotide delivery with polyhexylcyanoacrylate nanoparticles as carriers. Methods, 18: 286-95 (1999).

Zimmerman et al., A novel silver(I)-mediated DNA base pair. *J. Am. Chem. Soc.*, 124: 13684-5 (2002).

Non-Final Office Action issued in connection with U.S. Appl. No. 12/684,836, dated Jan. 6, 2012.

Final Office Action issued in connection with U.S. Appl. No. 11/917,680, dated Nov. 10, 2010.

Non-Final Office Action issued in connection with U.S. Appl. No. 11/917,680, dated Jun. 8, 2011.

Final Office Action issued in connection with U.S. Appl. No. 11/917,680, dated Nov. 10, 2011.

Non-Final Office Action issued in connection with U.S. Appl. No. 12/130,643, dated Jan. 13, 2011.

Non-Final Office Action issued in connection with U.S. Appl. No. 12/724,395, dated Feb. 17, 2012.
Final Office Action issued in connection with U.S. Appl. No. 12/130,643, dated Jun. 16, 2011.
International Search Report and Written Opinion for International Application No. PCT/US2006/022325, dated Oct. 20, 2006.
International Preliminary Report on Patentability for International Application No. PCT/US2006/022325, dated Dec. 17, 2007.
International Search Report and Written Opinion for International Application No. PCT/US2008/065366, dated Aug. 28, 2008.
International Preliminary Report on Patentability for International Application No. PCT/US2008/065366, dated Dec. 1, 2009.
International Search Report and Written Opinion for International application No. PCT/US2008/065822, dated Mar. 5, 2010.
International Preliminary Report on Patentability for International application No. PCT/US2009/065822, dated May 24, 2011.
International Search Report and Written Opinion for International Application No. PCT/US2010/044844, dated Apr. 27, 2011.
International Preliminary Report on Patentability for International Application No. PCT/US2010/044844, dated Feb. 7, 2012.
International Search Report and Written Opinion for International Application No. PCT/US2010/044453, dated Apr. 29, 2011.
International Preliminary Report on Patentability for International Application No. PCT/US2010/044453, dated Feb. 7, 2012.
International Search Report and Written Opinion for International Application No. PCT/US2010/27363, dated Apr. 15, 2010.
International Preliminary Report on Patentability, PCT/US2010/27363, dated Oct. 18, 2011.
International Search Report and Written Opinion for International Application No. PCT/US2010/47591, dated Oct. 4, 2010.
International Preliminary Report on Patentability, PCT/US2010/47591, dated Mar. 6, 2012.
International Search Report and Written Opinion for International Application No. PCT/US2010/47594, dated Oct. 8, 2010.
International Preliminary Report on Patentability, PCT/US2010/47594, dated Mar. 6, 2012.
International Search Report and Written Opinion for International Application No. PCT/US2010/020558, dated Mar. 9, 2010.
International Preliminary Report on Patentability for International Application No. PCT/US2010/020558, dated Jul. 12, 2011.
Agasti et al., Photoregulated release of caged anticancer drugs from gold nanoparticles, *J. Am. Chem. Soc.*, 131(16):5728-9 (2009).
Aime et al., Insights into the use of paramagnetic Gd(III) complexes in MR-molecular imaging investigations, J. Magn. Reson. Imaging, 16(4):394-406 (2002).
Aime et al., Pushing the sensitivity envelope of lanthanide-based magnetic resonance imaging (MRI) contrast agents for molecular imaging applications, Acc. Chem. Res., 42(7):822-31 (2009).
Alric et al., Gadolinium chelate coated gold nanoparticles as contrast agents for both X-ray computed tomography and magnetic resonance imaging, J. Am. Chem. Soc., 130(18):5908-15 (2008).
Biancone et al., Magnetic resonance imaging of gadolinium-labeled pancreatic islets for experimental transplantation, NMR Biomed., 20(1):40-8 (2007).
Bowman et al., Inhibition of HIV fusion with multivalent gold nanoparticles, J. Am. Chem. Soc., 130(22):6896-7 (2008).
Caravan et al., The interaction of MS-325 with human serum albumin and its effect on proton relaxation rates, J. Am. Chem. Soc., 124(12):3152-62 (2002).
Caravan, Strategies for increasing the sensitivity of gadolinium based MRI contrast agents, Chem. Soc. Rev., 35(6):512-23 (2006).
Chirila et al., The use of synthetic polymers for delivery of therapeutic antisense oligodeoxynucleotides. *Biomaterials*, 23: 321-42 (2002).
Crich et al., Improved route for the visualization of stem cells labeled with a Gd-/Eu-chelate as dual (MRI and fluorescence) agent, Magn. Reson. Med., 51(5):938-44 (2004).
Crooke et al., Progress in antisense technology. *Ann. Rev. Med.*, 55: 61-95 (2004).
Debouttiere et al., Adv. Funct. Mater., 16:2330 (2006).
Duimstra et al., A gadolinium chelate for detection of beta-glucuronidase: a self-immolative approach, J. Am. Chem. Soc., 127(37):12847-55 (2005).

Dykxhoorn et al., Killing the messenger: short RNAs that silence gene expression, Nat. Rev. Mol. Cell Biol., 4(6):457-67 (2003).
Frullano et al., Multimodal MRI contrast agents, J. Biol. Inorg. Chem., 12(7):939-40 (2007).
Han et al., A gold nanoparticle based approach for screening triplex DNA binders, J. Am. Chem. Soc., 128(15):4954-5 (2006).
Holen et al., Positional effects of short interfering RNAs targeting the human coagulation trigger tissue factor. *Nucl. Acids Res.*, 30: 1757-66 (2002).
Hu et al., Advances in high-field magnetic resonance imaging, Annu. Rev. Biomed.Eng., 6:157-84 (2004).
Kalman et al., Potentiometric and relaxometric properties of a gadolinium-based MRI contrast agent for sensing tissue pH, Inorg. Chem., 46(13):5260-70 (2007).
Kim et al., Biodegradable quantum dot nanocomposites enable live cell labeling and imaging of cytoplasmic targets, Nano Lett., 8(11):3887-92 (2008).
Lee et al., Colorimetric detection of mercuric ion (Hg2+) in aqueous media using DNA-functionalized gold nanoparticles, Angew. Chem. Int. Ed. Engl., 46(22):4093-6 (2007).
Li et al., A calcium-sensitive magnetic resonance imaging contrast agent. J. Am. Chem. Soc., 121:1413 (1999).
Liu et al., Rational design of "turn-on" allosteric DNAzyme catalytic beacons for aqueous mercury ions with ultrahigh sensitivity and selectivity, Angew. Chem. Int. Ed. Engl., 46(60):7587-90 (2007).
Major et al., The synthesis and in vitro testing of a zinc-activated MRI contrast agent, Proc. Natl. Acad. Sci. USA, 104(35):13881-6 (2007).
Mattson et al., A practical approach to crosslinking. *Molec. Biol. Rep.*, 17: 167-83 (1993).
Mendell, MicroRNAs: critical regulators of development, cellular physiology and malignancy, Cell Cycle, 4(9):1179-84 (2005).
Mittal, Improving the efficiency of RNA interference in mammals, Nat. Rev. Genet., 5(5):355-65 (2004).
Modo et al., Mapping transplanted stem cell migration after a stroke: a serial, in vivo magnetic resonance imaging study, Neuroimage, 21(1):311-7 (2004).
Moriggi et al., Gold nanoparticles functionalized with gadolinium chelates as high-relaxivity MRI contrast agents, J. Am. Chem. Soc., 131(31):10828-9 (2009).
Park et al., Gold nanoparticles functionalised by Gd-complex of DTPA-bis(amide) conjugate of glutathione as an MRI contrast agent, Bioorg. Med. Chem. Lett., 18(23):6135-7 (2008).
Penn et al., Nanoparticles for bioanalysis. Curr. Opin. Chem. Biol., 7: 609-15 (2003).
Perlette et al., Real-time monitoring of intracellular mRNA hybridization inside single living cells. Anal. Chem., 73: 5544-50 (2001).
Rethore et al., Preparation of chitosan/polyglutamic acid spheres based on the use of polystyrene template as nonviral gene carrier. *Tissue Engineering*, 15(4): 605-13 (2009).
Smith et al., Bioconjugated quantum dots for in vivo molecular and cellular imaging, Adv. Drug Deliv. Rev., 60(11):1226-40 (2008).
Song et al., Synthesis of multimeric MR contrast agents for cellular imaging, J. Am. Chem. Soc., 130(21):6662-3 (2008).
Taton et al., Scanometric DNA array detection with nanoparticle probes, Science, 289(5485):1757-60 (2000).
Virmani et al., Comparison of two different methods for inoculating VX2 tumors in rabbit livers and hind limbs, J. Vasc. Interv. Radiol., 19(6):931-6 (2008).
Wang et al., Superparamagnetic sub-5 nm Fe@C nanoparticles: isolation, structure, magnetic properties, and directed assembly, Nano Lett., 8(11):3761-5 (2008).
Xia, Nanomaterials at work in biomedical research, Nat. Mater., 7(10):758-60 (2008).
Xu et al., A gold-nanoparticle-based real-time colorimetric screening method for endonuclease activity and inhibition, Angew. Chem. Int. Ed. Engl., 46(19):3468-70 (2007).
Xu et al., Homogeneous detection of nucleic acids based upon the light scattering properties of silver-coated nanoparticle probes, Anal. Chem., 79(17):6650-4 (2007).
Zhang et al., PowerBlast: A new network Blast application for interactive or automated sequence analysis and annotation. Genome, 7: 649-56 (1997).

Non-Final Office Action issued in connection with U.S. Appl. No. 12/684,836, dated May 17, 2012.
Notice of Allowance issued in connection with U.S. Appl. No. 11/917,680, dated Apr. 26, 2012.
Non-Final Office Action issued in connection with U.S. Appl. No. 12/625,537, dated May 23, 2012.
European Examination Report from corresponding European Application No. 08729548.1, dated Jan. 19, 2010.
International Search Report and Written Opinion for International Application No. PCT/US2008/053603, dated Jul. 30, 2008.
International Search Report and Written Opinion for International Application No. PCT/US2010/55018, dated Dec. 9, 2010.
International Preliminary Report on Patentability for Itnernational Application No. PCT/US2010/55018, dated May 1, 2012.
Chompoosor et al., Charge Dependence of Ligand Release and Monolayer Stability of Gold Nanoparticles by Biogenic Thiols. *Bioconjugate Chem* 19: 1342-1345 (2008).
You et al., Detection and identification of proteins using nanoparticle-fluorescent polymer 'chemical nose' sensors. *Nature Nanotechnology* 2: 318-323 (2007).
Nitin, et al. "Oligonucleotide-Coated Metallic Nanoparticles as a Flexible Platform for Molecular Imaging Agents," Bioconjugate Chem. 18:2090-2096 (2007).

* cited by examiner

SEQUENCE LISTING

```
<160> NUMBER OF SEQ ID NOS: 13

<210> SEQ ID NO 1
<211> LENGTH: 23
<212> TYPE: DNA
<213> ORGANISM: Artificial sequence
<220> FEATURE:
<223> OTHER INFORMATION: Synthetic polynucleotide
<220> FEATURE:
<221> NAME/KEY: Misc_feature
<222> LOCATION: (23)..(23)
<223> OTHER INFORMATION: nucleotide at position 23 is thiolated

<400> SEQUENCE: 1
cttgagaaag ggctgccaaa aaa                                           23

<210> SEQ ID NO 2
<211> LENGTH: 10
<212> TYPE: DNA
<213> ORGANISM: Artificial sequence
<220> FEATURE:
<223> OTHER INFORMATION: Synthetic polynucleotide
<220> FEATURE:
<221> NAME/KEY: Misc_feature
<222> LOCATION: (1)..(1)
<223> OTHER INFORMATION: nucleotide at position 1 is tagged with Cy5

<400> SEQUENCE: 2
ttggcagccc                                                          10

<210> SEQ ID NO 3
<211> LENGTH: 18
```

```
<212> TYPE: DNA
<213> ORGANISM: Artificial sequence
<220> FEATURE:
<223> OTHER INFORMATION: Synthetic polynucleotide

<400> SEQUENCE: 3
tggcagccct ttctcaag                                                     18

<210> SEQ ID NO 4
<211> LENGTH: 23
<212> TYPE: DNA
<213> ORGANISM: Artificial sequence
<220> FEATURE:
<223> OTHER INFORMATION: Synthetic polynucleotide
<220> FEATURE:
<221> NAME/KEY: Misc_feature
<222> LOCATION: (23)..(23)
<223> OTHER INFORMATION: nucleotide at position 23 is thiolated

<400> SEQUENCE: 4
ctatcgcgta caatctgcaa aaa                                               23

<210> SEQ ID NO 5
<211> LENGTH: 13
<212> TYPE: DNA
<213> ORGANISM: Artificial sequence
<220> FEATURE:
<223> OTHER INFORMATION: Synthetic polynucleotide
<220> FEATURE:
<221> NAME/KEY: Misc_feature
<222> LOCATION: (1)..(1)
<223> OTHER INFORMATION: nucleotide at position 1 is tagged with Cy5

<400> SEQUENCE: 5
tgcagattgt acg                                                          13

<210> SEQ ID NO 6
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 6
tcttcttcaa ggacgacggc aact                                              24

<210> SEQ ID NO 7
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 7
tgtggcggat cttgaagttc acct                                              24

<210> SEQ ID NO 8
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 8
tcttcttcaa ggacgacggc aact                                              24

<210> SEQ ID NO 9
<211> LENGTH: 24
```

-continued

```
<212> TYPE: DNA
<213> ORGANISM: Artificial sequence
<220> FEATURE:
<223> OTHER INFORMATION: Synthetic polynucleotide

<400> SEQUENCE: 9
tgtggcggat cttgaagttc acct                                              24

<210> SEQ ID NO 10
<211> LENGTH: 52
<212> TYPE: DNA
<213> ORGANISM: Artificial sequence
<220> FEATURE:
<223> OTHER INFORMATION: Synthetic polynucleotide

<400> SEQUENCE: 10
tgcataatac gactcactat agggagatct tcttcaagga cgacgggcaa ct              52

<210> SEQ ID NO 11
<211> LENGTH: 18
<212> TYPE: DNA
<213> ORGANISM: Artificial sequence
<220> FEATURE:
<223> OTHER INFORMATION: Synthetic polynucleotide

<400> SEQUENCE: 11
atgggtgccc cgacgttg                                                    18

<210> SEQ ID NO 12
<211> LENGTH: 18
<212> TYPE: DNA
<213> ORGANISM: Artificial sequence
<220> FEATURE:
<223> OTHER INFORMATION: Synthetic polynucleotide

<400> SEQUENCE: 12
agaggcctca atccatgg                                                    18

<210> SEQ ID NO 13
<211> LENGTH: 44
<212> TYPE: DNA
<213> ORGANISM: Artificial sequence
<220> FEATURE:
<223> OTHER INFORMATION: Synthetic polynucleotide

<400> SEQUENCE: 13
tgcataatac gactcactat agggagatgg gtgccccgac gttg                       44
```

PARTICLES FOR DETECTING INTRACELLULAR TARGETS

CROSS-REFERENCE TO RELATED APPLICATIONS

This application is the U.S. national phase of International Application No. PCT/US2008/053603, filed Feb. 11, 2008, which claims the priority benefit under 35 U.S.C. §119(e) of U.S. Provisional Application No. 60/900,648, filed Feb. 9, 2007 and U.S. Provisional Application No. 60/956,205, filed Aug. 16, 2007, the disclosures of which are incorporated herein by reference in their entirety.

GRANT FUNDING DISCLOSURE

This invention was made with government support under grant numbers IU54-CA 119341, awarded by the Cancer Center for Nanotechnology Excellence (NCI/CCNE) and 5DPIOD000285, awarded from a NIH Director's Pioneer Award, and grant number EEC-0647560, awarded by the NSEC. The government has certain rights in the invention.

FIELD OF THE INVENTION

The present invention relates to methods of detecting the intracellular concentration of a target molecule using a nanoparticle wherein the nanoparticle comprises a binding moiety that can specifically associate with the target molecule, and wherein said association results in a change in a detectable marker that can be measured after association with the target molecule.

BACKGROUND OF THE INVENTION

Labeled oligonucleotides are widely used probes for detecting specific macromolecule targets such as nucleic acids and proteins. Their ability to bind targets with high specificity has rendered them useful in in vitro assays such as polymerase chain reaction (PCR) protocols. However, delivering these types of target specific probes into living cells remains a major challenge as cells are both naturally resistant to nucleic acid uptake and contain a variety of pathways to remove these foreign genetic materials. Thus, methods that deliver these materials into cells, in a manner in which they retain both their specific binding properties and fluorescent signaling ability are of great interest.

The discovery and subsequent development of the oligonucleotide-nanoparticle conjugate have lead to a variety of new opportunities in molecular diagnostics (Elghanian et al., 1997, *Science* 277: 1078-1081; Nam et al., 2003, *Science* 308: 1884-1886) and materials design (Mirkin et al., 1996, *Nature* 382: 607-609; Alivisatos et al., 1996, *Nature* 382: 609-611; Demers et al., 2003, *Angew. Chem. Int. Ed.* 40: 3071-3073). Recently, it has been demonstrated that oligonucleotide-functionalized nanoparticles enter cells and act as antisense agents to control gene expression (Rosi et al., 2006, *Science* 312: 1027-1030). These "antisense particles" are not simply delivery vehicles (Sandhu et al., 2002, *Bioconjugate Chem.* 13: 3-6; Tkachenko et al., 2003, *J. Am. Chem. Soc.* 125: 4700-4701), but rather single entity regulation and transfection agents that undergo cellular internalization, resist enzymatic degradation, and bind intracellular targets with affinity constants that are as much as two orders of magnitude greater than free oligonucleotides (Lytton-Jean and Mirkin, 2005, *J. Am. Chem. Soc.* 127: 12754-12755). Moreover, they can be easily modified with potent, i.e., highly stable, designer materials such as locked nucleic acids (Seferos et al., 2007, *Chem Bio Chem* 8: 1230-1232) and are nontoxic under conditions required for gene regulation. Indeed, it has been shown that, unlike oligonucleotides free in solution, oligonucleotide-modified gold nanoparticles are readily taken up by cells in high numbers. This property has lead to the discovery that oligonucleotide-modified gold nanoparticles can be used as agents for intracellular gene control, where they provide rapid intracellular delivery of DNA, and further increase the efficacy of the oligonucleotides in the cells based on cooperative properties. These oligonucleotide functionalized nanoparticles have been shown to enter a variety of cell types, and can be used to introduce high local concentrations of oligonucleotides.

It has also previously been shown that gold nanoparticles that are densely functionalized with DNA bind complementary DNA in a highly cooperative manner, resulting in a binding strength that is two orders-of-magnitude greater than that determined for analogous DNA strands that are not attached to a gold nanoparticle. This property has rendered nanoparticles particularly useful for DNA and protein diagnostic assays in addition to those uses described above.

One class of oligonucleotides of interest are those that can detect a specific target with a recognition sequence. These types of structures, if introduced into living cells, are especially of interest for medical diagnosis, drug discovery, and developmental and molecular biology application. However, current delivery/transfection strategies lack the attributes required for their use such as 1) low toxicity, 2) high cellular uptake, and 3) provide resistance to enzymes that lead to false positive signals.

Probes to visualize and detect intracellular RNA including those used for in situ staining (Femino et al., *Science* 280: 585-590, 1998; Kloosterman et al., *Nat. Methods* 3: 27-29, 2006), molecular beacons (Tyagi et al., 1996, *Nat. Biotechnol.* 14: 303-308; Sokol et al., 1998, *Proc. Natl. Acad. Sci. USA* 95: 11538-11543; Peng et al., 2005, *Cancer Res.* 65: 1909-1917; Perlette et al., 2001, *Anal. Chem.* 73: 5544-5550; Nitin et al., 2004, *Nucleic Acids Res.* 32: e58), and FRET-pairs (Santangelo et al., 2004, *Nucleic Acids Res.* 32: e57; Bratu et al., 2003, *Proc. Natl. Acad. Sci. USA* 100: 3308-13313) each of which are important biological tools to measure and quantify activity in living systems in response to external stimuli (Santangelo et al., 2006, *Annals of Biomedical Engineering* 34: 39-50). However, the delivery of oligonucleotide-based reporters into cellular media and cells has proven to be a major challenge for intracellular detection. The cellular internalization of oligonucleotide-based probes typically requires transfection agents such as lipids (Zabner et al., 1995, *J. Bio. Chem.* 270: 18997-19007) or dendrimers (Kukowska-Latallo et al., 1996, *Proc. Natl. Acad. Sci. USA* 93: 4897-4902) which can be toxic or alter cellular processes. Furthermore, oligonucleotides are prone to degradation within cells (Opalinska and Gewirtz, 2002, *Nat. Rev. Drug Disc.* 1: 503-514), and in the case of fluorophore-labeled probes, this can lead to a high background signal that is indistinguishable from a true recognition event (Li et al., 2004, *Nucleic Acids Res.* 28: e52; Rizzo et al., 2002, *Molecular and Cellular Probes* 16: 277-283).

Accordingly, while nanoparticle have been designed that can recognize targets with a high degree of specificity, it is difficult to detect a positive effect arising from the specific interaction, particularly with the sensitivity to detect such an interaction at the single cell level.

Thus there exists a need in the art to develop materials which are capable of entering a cell to associate with a specific target and methods to detect and quantitate the resulting intracellular interaction.

SUMMARY OF THE INVENTION

Provided here are methods of determining the intracellular concentration of a target molecule comprising the step of contacting the target molecule with a nanoparticle under conditions that allow association of the target molecule with the nanoparticle, the nanoparticle comprising a binding moiety specific for said target molecule, the binding moiety labeled with a marker, wherein the association of the target molecule and the nanoparticle results in detectable change in the marker, and wherein the change in the detectable marker is proportional to the intracellular concentration of said target molecule.

In one embodiment of the methods, the binding moiety is a polynucleotide and in another aspect, the binding moiety is a polypeptide. In the embodiment wherein the binding moiety is a polynucleotide, alternative aspects include those in which the binding moiety is a DNA molecule or an RNA molecule. In other embodiments of the methods, the target molecule is a polynucleotide or a polypeptide. In the embodiment wherein the target molecule is a polynucleotide, alternative aspects include those in which the binding moiety which is a DNA molecule or an RNA molecule.

In one embodiment, methods are provided wherein the binding moiety is a polynucleotide covalently attached to the nanoparticle and the marker is a label attached to a polynucleotide hybridized to the binding moiety polynucleotide, wherein association of the binding moiety polynucleotide with the target molecule releases the hybridized polynucleotide and the marker is detectable after release. In one aspect, the marker is attached to the hybridized polynucleotide and the marker is quenched when the hybridized polynucleotide with the marker is hybridized to the binding moiety.

In another embodiment, methods are provided wherein the binding moiety is a polypeptide covalently attached to the nanoparticle and the marker is a label attached to an agent associated with the binding moiety polypeptide, wherein association of the binding moiety polypeptide with the target molecule displaces the associated agent and the marker is detectable after release. In one aspect, the marker is attached to the agent and the marker is quenched when the agent is associated with the binding moiety polypeptide.

In another embodiment, methods are provided wherein the binding moiety is labeled with a marker and the marker is detectable only when binding moiety is associated with the target molecule. In the embodiment wherein the binding moiety is a polynucleotide, alternative aspects include those in which the binding moiety is a DNA molecule or an RNA molecule. In other embodiments of the methods, the target molecule is a polynucleotide or a polypeptide. In the embodiment wherein the target molecule is a polynucleotide, alternative aspects include those in which the binding moiety which is a DNA molecule or an RNA molecule.

In one aspect, the binding moiety is a polynucleotide and the marker is attached to the polynucleotide binding moiety such that the marker is quenched when the polynucleotide binding moiety is not associated with the target molecule. Accordingly, the marker attached to the polynucleotide binding moiety is detectable only when the polynucleotide binding moiety is associated with the target molecule.

In another aspect, the binding moiety is a polypeptide and the marker is attached to polypeptide binding moiety such that the marker is quenched when the polypeptide binding moiety is not associated with the target molecule. Accordingly, the marker attached to the polypeptide binding moiety is detectable only when the polypeptide biding moiety is associated with the target molecule.

Also provided are methods wherein said nanoparticle comprises a multiplicity of binding moieties. In one aspect, methods are provided wherein the multiplicity of binding moieties specifically associate with one target molecule. In another aspect, the multiplicity binding moieties specifically associate with more than one target molecule.

Further aspects of the invention will become apparent from the detailed description provided below. However, it should be understood that the following detailed description and examples, while indicating preferred embodiments of the invention, are given by way of illustration only since various changes and modifications within the spirit and scope of the invention will become apparent to those skilled in the art from this detailed description.

DETAILED DESCRIPTION OF THE INVENTION

Figure 1:
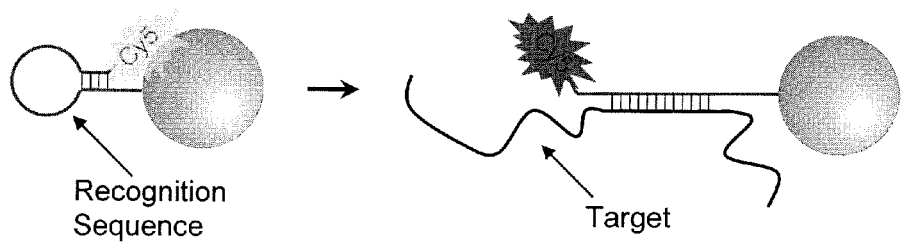
FIG. 1 provides a scheme for the gold nanoparticles modified with a fluorophore containing oligonucleotide that is capable of detecting an intracellular target.

Methods provided herein exploit the physical properties and applications of nanoparticles modified to include one or more binding moieties that specifically recognize and associate with one or more specific target moieties. It is shown herein that intracellular concentrations of target molecules can be determined using nanoparticles that comprise a binding moiety that is specific for the target molecule. In the present invention the binding moiety is labeled with a marker wherein the association of the target molecule and the nanoparticle results in detectable change in the marker, and wherein the change in the detectable marker is proportional to the intracellular concentration of said target molecule. It will be appreciated that the intracellular target includes those which are naturally occurring in the target cell, those which are naturally occurring targets that have been introduced into the cell (but are not ordinarily found in that cell type) or synthetic targets which do not occur in nature but have been introduced into the target cell.

In another aspect of the present invention, the intracellular localization of a desired target may also be determined using the methods outlined herein.

As used herein, the term "binding moiety" is understood to encompass a polynucleotide or a polypeptide, or any other fragment or segment of any of the preceding molecules that can associate with a target of interest. This term includes, but is not limited to, small molecules of interest. As is understood in the art, the term "small molecule" includes organic and inorganic compounds which are either naturally-occurring compounds, modifications of naturally-occurring compounds, or synthetic compounds.

The methods provided are particularly amenable to use of binding moieties which recognize and associate with intracellular target molecules, wherein the binding moieties are polynucleotides and/or polypeptides, and the target molecules are polynucleotides and/or polypeptides. In a simple aspect, a polynucleotide binding moiety specifically associates with a polynucleotide target molecule or a polypeptide binding moiety specifically associates with a polypeptide target molecule. However, methods are also contemplated wherein a polynucleotide binding moiety specifically associates with a polypeptide target molecule or a polypeptide binding moiety specifically associates with a polynucleotide target molecule.

As used herein, the term "specifically recognizes" or "specifically associates" means that the binding moiety can identify and/or interact with one target molecule with a higher affinity and/or avidity compared to all other target molecules.

The methods provided function under the principle that the binding moiety is directly or indirectly labeled with a marker, and association of the binding moiety with the target molecule results in the marker becoming detectable, or more detectable. Accordingly, when the binding moiety is not associated with the target molecule, the marker is relatively undetectable, or quenched. While it is understood in the art that the term "quench" or "quenching" is often associated with fluorescent markers, it is contemplated herein that the signal of any marker that is quenched when it is relatively undetectable. Thus, it is to be understood that methods exemplified throughout this description that employ fluorescent markers are provided only as single embodiments of the methods contemplated, and that any marker which can be quenched can be substituted for the exemplary fluorescent marker.

In one aspect, the marker is a label attached directly to the binding moiety, and in another aspect, the marker is a label attached to an agent associated with the binding moiety, this agent having a lower binding affinity or binding avidity for the binding moiety such that association of the target molecule with the binding moiety causes the agent to be displaced from its association with the binding moiety.

When the marker is attached directly to the binding moiety, the marker is positioned such that it is relatively undetectable or quenched when the binding moiety is not associated with a target molecule. For example, with a polynucleotide binding moiety that is not associated with a target molecule, the marker can be positioned in proximity to the nanoparticle itself through either secondary structure which forms within the polynucleotide binding moiety, or the marker can be freely wavering in the aqueous environment such that at any given time the marker can be in proximity to the nanoparticle and its signal quenched or freely wavering (though still tethered to the nanoparticle) in the aqueous environment at a distance from the nanoparticle that the signal is not quenched. In this embodiment wherein no secondary structure holds the marker in a quenched position in proximity to the nanoparticle when the polynucleotide binding moiety is not in association with a target molecule, a level of background signal will necessarily be detected, and association of the polynucleotide binding moiety with a target molecule will strengthen the signal over background as a result of the fact that more marker with be displaced from sufficient proximity to the nanoparticle to impart a quenching effect.

Similarly when the binding moiety is a polypeptide, the marker on the binding moiety may be positioned such that a conformation change that occurs when the polypeptide binding moiety is in association with a target molecule results in the marker moving sufficiently away from the nanoparticle that its signal is relatively unquenched.

In aspects of the methods wherein the marker is indirectly associated with the binding moiety, association of the binding moiety with a target molecule cause a physical release of the marker such that the nanoparticle is no longer able to exert a quenching effect on the marker. For example, with a polynucleotide binding moiety, the marker may be labeled on a second polynucleotide which can hybridize to the polynucleotide binding moiety in a position such that the marker is in sufficient proximity to the nanoparticle that the nanoparticle exerts its quenching effect. When the polynucleotide binding molecule recognizes and associates with a target molecule, the hybridized and labeled polynucleotide is displaced, and the quenching effect of the nanoparticle is abated.

Thus, in one aspect for example, methods are provided wherein gold nanoparticle modified to include a polynucleotide binding moiety which in turn is hybridized to complementary polynucleotide labeled with a fluorophore marker can be used as both transfection agents and cellular "nano-flares" for visualizing and quantifying RNA in living cells. Nano-flares take advantage of the highly efficient fluorescence quenching properties of gold (Dubertret et al., 2001, Nat. Biotechnol. 19: 365-370), cellular uptake of oligonucleotide nanoparticle conjugates without the use of transfection agents, and the enzymatic stability of such conjugates (Rosi et al., 2006, Science 312: 1027-1030), thus overcoming many of the challenges to creating sensitive and effective intracellular probes. Specifically, nano-flares exhibit high signaling, have low background fluorescence, and are sensitive to changes in the number of RNA transcripts present in cells. Thus, the nano-flares described herein are oligonucleotide functionalized nanoparticle conjugates designed to provide an intracellular fluorescence signal that directly or indirectly correlates with the relative amount of a specific intracellular RNA. RNA contemplated for detection in the disclosed methods include, but are not limited to, mRNA and hnRNA.

A similar mechanism operates for a polypeptide binding moiety, wherein an agent labeled with a marker and the agent is able to associate with the polypeptide binding moiety in such a way that its association brings the agent and marker sufficiently close to the nanoparticle that the marker is relatively quenched. When the polypeptide binding moiety associates with a specific target molecule, the agent is released or displaced as with the nano-flare described above and the quenching effect of the nanoparticle is relieved.

Regardless of the specific nature of the binding moiety, by utilizing nanoparticles densely functionalized with fluorophore-labeled oligonucleotides or polypeptides, several difficulties commonly associated with intracellular molecule detection are alleviated. These binding moieties do not require microinjection or auxiliary transfection reagents to enter cells, are highly resistant towards enzymatic degradation and are non-toxic under the conditions studied.

Polynucleotides

As used herein, the term in "polynucleotide," either functionalized on a nanoparticle or as a target molecule, is used interchangeably with the term oligonucleotide.

The term "nucleotide" or its plural as used herein is interchangeable with modified forms as discussed herein and otherwise known in the art. In certain instances, the art uses the term "nucleobase" which embraces naturally-occurring nucleotides as well as modifications of nucleotides that can be polymerized.

Methods of making polynucleotides of a predetermined sequence are well-known in the art. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

In various aspects, methods provided include use of polynucleotides which are DNA oligonucleotides, RNA oligonucleotides, or combinations of the two types. Modified forms of oligonucleotides are also contemplated which include those having at least one modified internucleotide linkage. Modified polynucleotides or oligonucleotides are described in detail herein below.

Modified Oligonucleotides

Specific examples of oligonucleotides include those containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone are considered to be within the meaning of "oligonucleotide."

Modified oligonucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are oligonucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated. Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

In still other embodiments, oligonucleotide mimetics wherein both one or more sugar and/or one or more internucleotide linkage of the nucleotide units are replaced with "non-naturally occurring" groups. In one aspect, this embodiment contemplates a peptide nucleic acid (PNA). In PNA compounds, the sugar-backbone of an oligonucleotide is replaced with an amide containing backbone. See, for example U.S. Pat. Nos. 5,539,082; 5,714,331; and 5,719,262, and Nielsen et al., 1991, *Science,* 254: 1497-1500, the disclosures of which are herein incorporated by reference.

In still other embodiments, oligonucleotides are provided with phosphorothioate backbones and oligonucleosides with heteroatom backbones, and including —$CH_2$—NH—O—$CH_2$—, —$CH_2$—N($CH_3$)—O—$CH_2$—, —$CH_2$—O—N($CH_3$)—$CH_2$—, —$CH_2$—N($CH_3$)—N($CH_3$)—$CH_2$— and —O—N($CH_3$)—$CH_2$—$CH_2$— described in U.S. Pat. Nos. 5,489,677, and 5,602,240. Also contemplated are oligonucleotides with morpholino backbone structures described in U.S. Pat. No. 5,034,506.

In various forms, the linkage between two successive monomers in the oligo consists of 2 to 4, desirably 3, groups/atoms selected from —$CH_2$—, —O—, —S—, —$NR^H$—, >C=O, >C=$NR^H$, >C=S, —Si(R")$_2$—, —SO—, —S(O)$_2$—, —P(O)$_2$—, —PO(BH$_2$)—, —P(O,S)—, —P(S)$_2$—, —PO(R")—, —PO(OCH$_3$)—, and —PO(NHR$^H$)—, where RH is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH= (including $R^5$ when used as a linkage to a succeeding monomer), —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—O—CO—O—, —O—CO—$CH_2$—O—, —O—$CH_2$—CO—O—, —$CH_2$—CO—$NR^H$—, —O—CO—$NR^H$—, —$NR^H$CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N=(including $R^5$ when used as a linkage to a succeeding monomer), $CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$, —O—$CH_2$—S—, —S—$CH_2$—O—, —$CH_2$—$CH_2$S—, —O—$CH_2$—$CH_2$—S—, —S—$CH_2$—CH=(including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—SO$_2$—$CH_2$—, —O—SO—O—, —O—S(O)$_2$—O—, —O—S(O)$_2$—$CH_2$—, —O—S(O)$_2$—$NR^H$—, —$NR^H$—S(O)$_2$—$CH_2$; —O—S(O)$_2$—$CH_2$—, —O—P(O)$_2$—O—, —P(O,S)—O—, —O—P(S)$_2$—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(OCH$_2$CH$_2$S—R)—O—, —O—PO(BH$_3$)—O—, —O—PO(NHR$^N$)—O—, —O—P(O)$_2$—$NR^H$H—, —$NR^H$—P(O)$_2$—O—, —O—P(O,$NR^H$)—O—, —$CH_2$—P(O)$_2$—O—, —O—P(O)$_2$—$CH_2$—, and —O—Si(R")$_2$—O—; among which —$CH_2$—CO—

NR$^H$—, —CH$_2$—NR$^H$—O—, —S—CH$_2$—O—, —O—P(O)$_2$—O—O—P(—O,S)—O—, —O—P(S)$_2$—O—, —NR$^H$ P(O)$_2$—O—, —O—P(O,NR$^H$)—O—, —O—PO(R")—O—, —O—PO(CH$_3$)—O—, and —O—PO(NHR$^N$)—O—, where RH is selected form hydrogen and C$_{1-4}$-alkyl, and R" is selected from C$_{1-6}$-alkyl and phenyl, are contemplated. Further illustrative examples are given in Mesmaeker et. al., 1995, *Current Opinion in Structural Biology*, 5: 343-355 and Susan M. Freier and Karl-Heinz Altmann, 1997, *Nucleic Acids Research*, vol 25: pp 4429-4443.

Still other modified forms of oligonucleotides are described in detail in U.S. patent application NO. 20040219565, the disclosure of which is incorporated by reference herein in its entirety.

Modified oligonucleotides may also contain one or more substituted sugar moieties. In certain aspects, oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Other embodiments include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$]$_2$, where n and m are from 1 to about 10. Other oligonucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one aspect, a modification includes T-methoxyethoxy(2'-O—CH$_2$CH$_2$OCH$_3$, also known as 2'-O-(2-methoxyethyl) or 2'-MOE) (Martin et al., 1995, *Helv. Chim. Acta*, 78: 486-504) i.e., an alkoxyalkoxy group. Other modifications include 2'-dimethylaminooxyethoxy, i.e., a O(CH$_2$)$_2$ON(CH$_3$)$_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$, also described in examples herein below.

Still other modifications include 2'-methoxy(2'-O—CH$_3$), 2'-aminopropoxy(2'-OCH$_2$CH$_2$CH$_2$NH$_2$), 2'-allyl(2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. In one aspect, a 2'-arabino modification is 2'-F. Similar modifications may also be made at other positions on the oligonucleotide, for example, at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects is a methylene (—CH$_2$—)$_n$ group bridging the 2' oxygen atom and the 4' carbon atom wherein n is 1 or 2. LNAs and preparation thereof are described in WO 98/39352 and WO 99/14226.

Oligonucleotides may also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, *Angewandte Chemie*, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. No. 3,687,808, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,750,692 and 5,681,941, the disclosures of which are incorporated herein by reference.

A "modified base" or other similar term refers to a composition which can pair with a natural base (e.g., adenine, guanine, cytosine, uracil, and/or thymine) and/or can pair with a non-naturally occurring base. In certain aspects, the modified base provides a $T_m$ differential of 15, 12, 10, 8, 6, 4, or 2° C. or less. Exemplary modified bases are described in EP 1 072 679 and WO 97/12896.

By "nucleobase" is meant the naturally occurring nucleobases adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4,N^4$-ethanocytosin, N',N'-ethano-2,6-diaminopurine, 5-methylcytosine (mC), 5-($C^3$-$C^6$)-alkynyl-cytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, *Nucleic Acids Research*, vol. 25: pp 4429-4443. The term "nucleobase" thus includes not only the known purine and pyrimidine heterocycles, but also heterocyclic analogues and tautomers thereof Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, *Angewandte Chemie*, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). The term "nucleosidic base" or "base unit" is further intended to include compounds such as heterocyclic compounds that can serve like nucleobases including certain "universal bases" that are not nucleosidic bases in the most classical sense but serve as nucleosidic bases. Especially mentioned as universal bases are 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Polypeptides

As used herein, the term "polypeptide" refers to peptides, proteins, polymers of amino acids, hormones, viruses, and antibodies that are naturally derived, synthetically produced, or recombinantly produced. Polypeptides also include lipoproteins and post translationally modified proteins, such as, for example, glycosylated proteins, as well as proteins or protein substances that have D-amino acids, modified, derivatized, or non-naturally occurring amino acids in the D- or L-configuration and/or peptomimetic units as part of their structure.

Peptides contemplated for use in the methods provided include those derived from commercially available sources. Libraries include structured peptide libraries comprising small, disulfide-constrained cyclic peptide compounds that range in size from six to twelve amino acids, wherein the number of distinct peptide structures in each library typically exceeds 1 billion; (ii) linear peptide libraries wherein 19 amino acids (no cysteine) at each position in a 20-mer peptide are allowed to create a library of 10 billion peptides; (iii) substrate phage peptide libraries wherein all 19 amino acids (no cysteine) at each position in a 13-mer peptide are allowed to create a library of approximately 100 million peptides.

Commercially available peptide libraries include those from Peptide libraries Eurogentec s.a. (Belgium), Dyax Corp. (Cambridge, Mass.) and Cambridge Peptide (Cambridge, UK).

Preparation of peptide libraries useful in practice of the method is well known in the art, as described by Jung (ed) *Combinatorial Peptide and Nonpeptide Libraries: A Handbook* and in Devlin et al., 1990, *Science*, Vol 249, Issue 4967: 404-406, as well from use of commercially available synthesis kits from, for example, Sigma-Genosys.

Proteins contemplated for use in the methods provided include those derived from synthesized proteins libraries as described in Matsuura, et al., 2002, *Protein Science* 11: 2631-2643, Ohuchi et al., 1998, *Nucleic Acids Res.* October 1; 26(19): 4339-4346, WO/1999/011655, WO/1998/047343, U.S. Pat. No. 6,844,161 and U.S. Pat. No. 6,403,312. Commercially available kits for production of protein libraries are also know in the art and available from, for example, BioCat GmbH (Heidelberg).

Protein libraries useful in practice of the methods are also commercially available from, for example, Dyax Corp. (Cambridge, Mass.).

Detectable Marker/Label

A "marker" as used herein is interchangeable with "label" and regardless of the type of interacting compound being identified, methods are provided wherein polynucleotide or polypeptide complex formation is detected by an observable change. In one aspect, complex formation gives rise to a color change which is observed with the naked eye or spectroscopically. When using gold nanoparticles, a red-to-blue color change occurs with nanoparticle aggregation which often is detected with the naked eye. In the present invention, aggregation is contemplated to occur as a result of separate nanoparticles, each containing binding moieties to a specific but different portion of the target molecule, bind the same target molecule.

In another aspect, polynucleotide or polypeptide complex formation gives rise to aggregate formation which is observed by electron microscopy or by nephelometry. Aggregation of nanoparticles in general gives rise to decreased plasmon resonance. In still another aspect, complex formation gives rise to precipitation of aggregated nanoparticles which is observed with the naked eye or microscopically.

The observation of a color change with the naked eye is, in one aspect, made against a background of a contrasting color. For instance, when gold nanoparticles are used, the observation of a color change is facilitated by spotting a sample of the hybridization solution on a solid white surface (such as, without limitation, silica or alumina TLC plates, filter paper, cellulose nitrate membranes, nylon membranes, or a C-18 silica TLC plate) and allowing the spot to dry. Initially, the spot retains the color of the hybridization solution, which ranges from pink/red, in the absence of hybridization, to purplish-red/purple, if there has been hybridization. On drying at room temperature or 80° C. (temperature is not critical), a blue spot develops if the nanoparticle-oligonucleotide conjugates had been linked by hybridization prior to spotting. In the absence of hybridization, the spot is pink. The blue and the pink spots are stable and do not change on subsequent cooling or heating or over time providing a convenient permanent record of the test. No other steps (such as a separation of hybridized and unhybridized nanoparticle-oligonucleotide conjugates) are necessary to observe the color change.

An alternate method for visualizing the results from practice of the methods is to spot a sample of nanoparticle probes on a glass fiber filter (e.g., Borosilicate Microfiber Filter, 0.7 micron pore size, grade FG75, for use with gold nanoparticles 13 nm in size), while drawing the liquid through the filter. Subsequent rinsing washes the excess, non-hybridized probes through the filter, leaving behind an observable spot comprising the aggregates generated by hybridization of the nanoparticle probes (retained because these aggregates are larger than the pores of the filter). This technique allows for greater sensitivity, since an excess of nanoparticle probes can be used.

It will be understood that a marker contemplated will include any of the fluorophores described herein as well as other detectable markers known in the art. For example, markers also include, but are not limited to, redox active probes, other nanoparticles, and quantum dots, as well as any marker which can be detected using spectroscopic means, i.e., those markers detectable using microscopy and cytometry.

Methods of Labeling Oligonucleotides

Methods of labeling oligonucleotides with fluorescent molecules and measuring fluorescence are well known in the art. Suitable fluorescent molecules are also well known in the art and include without limitation 1,8-ANS (1-Anilinonaphthalene-8-sulfonic acid), 1-Anilinonaphthalene-8-sulfonic acid (1,8-ANS), 5-(and -6)-Carboxy-2',7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), BO-PRO-1-DNA, BO-PRO-3-DNA, BOBO-1-DNA, BOBO-3-DNA, BODIPY 650/665-X, MeOH, BODIPY FL conjugate, BODIPY FL, MeOH, Bodipy R6G SE, BODIPY R6G, MeOH, BODIPY TMR-X antibody conjugate pH 7.2, Bodipy TMR-X conjugate, BODIPY TMR-X, MeOH, BODIPY TMR-X, SE, BODIPY TR-X phallacidin pH 7.0, BODIPY TR-X, MeOH, BODIPY TR-X, SE, BOPRO-1, BOPRO-3, Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, Cy 5.5, CyQUANT GR-DNA, Dansyl Cadaverine, Dansyl Cadaverine, MeOH, DAPI, DAPI-DNA, Dapoxyl (2-aminoethyl)sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, Ethidium Bromide, Ethidium homodimer, Ethidium homodimer-1-DNA, eYFP (Enhanced Yellow Fluorescent Protein), FDA, FITC, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Co, Fura-2 Ca2+, Fura-2, high Ca Fura-2, no Cu, GFP (S65T), HcRed, Hoechst 33258, Hoechst 33258-DNA, Hoechst 33342, Indo-1 Ca2+, Indo-1, Ca free, Indo-1, Ca saturated, JC-1, JC-1 pH 8.2, Lissamine rhodamine, LOLO-1-DNA, Lucifer Yellow, CH, LysoSensor Blue, LysoSensor Blue pH 5.0, LysoSensor Green, LysoSensor Green pH 5.0, LysoSensor Yellow pH 3.0, LysoSensor Yellow pH 9.0, LysoTracker Blue, LysoTracker Green, LysoTracker Red, Magnesium Green, Magnesium Green Mg2+, Magnesium Orange, Marina Blue, mBanana, mCherry, mHoneydew, MitoTracker Green, MitoTracker Green FM, MeOH, MitoTracker Orange, MitoTracker Orange, MeOH, MitoTracker Red, MitoTracker Red, MeOH, mOrange, mPlum, mRFP, mStrawberry, mTangerine, NBD-X, NBD-X, MeOH, NeuroTrace 500/525, green fluorescent Nissl stain-RNA, Nile Blue, EtOH, Nile Red, Nile Red-lipid, Nissl, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, PicoGreen dsDNA quantitation reagent, PO-PRO-1, PO-PRO-1-DNA, PO-PRO-3, PO-PRO-3-DNA, POPO-1, POPO-1-DNA, POPO-3, Propidium Iodide, Propidium Iodide-DNA, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodaminen Green pH 7.0, Rhodol Green antibody conjugate pH 8.0, Sapphire, SBFI-Na+, Sodium Green Na+, Sulforhodamine 101, EtOH, SYBR Green I, SYPRO Ruby, SYTO 13-DNA, SYTO 45-DNA, SYTOX Blue-DNA, Tetramethylrhodamine antibody conjugate pH 8.0, Tetramethylrhodamine dextran pH 7.0, Texas Red-X antibody conjugate pH 7.2, TO-PRO-1-DNA, TO-PRO-3-DNA, TOTO-1-DNA, TOTO-3-DNA, TRITC, X-Rhod-1 Ca2+, YO-PRO-1-DNA, YO-PRO-3-DNA, YOYO-1-DNA, and YOYO-3-DNA.

In yet another embodiment, two types of fluorescent-labeled oligonucleotides attached to two different particles can be used as long as the nanoparticles have the ability to quench the detectable marker being utilized. Suitable particles include polymeric particles (such as, without limitation, polystyrene particles, polyvinyl particles, acrylate and methacrylate particles), glass particles, latex particles, Sepharose beads and others like particles well known in the art. Methods of attaching oligonucleotides to such particles are well known and routinely practiced in the art. See Chrisey et al., 1996, *Nucleic Acids Research*, 24: 3031-3039 (glass) and Charreyre et al., 1997 *Langmuir*, 13: 3103-3110, Fahy et al., 1993, *Nucleic Acids Research*, 21: 1819-1826, Elaissari et al., 1998, *J. Colloid Interface Sci.*, 202: 251-260, Kolarova et al., 1996, *Biotechniques*, 20: 196-198 and Wolf et al., 1987, *Nucleic Acids Research*, 15: 2911-2926 (polymer/latex).

Other labels besides fluorescent molecules can be used, such as chemiluminescent molecules, which will give a detectable signal or a change in detectable signal upon hybridization.

Nanoparticles

As used herein, "nanoparticle" refers to small structures that are less than 10 μm, and preferably less than 5 μm, in any one dimension. In general, nanoparticles contemplated include any compound or substance with a high loading capacity for an oligonucleotide as described herein. Nanoparticles useful in the practice of the invention include metal (e.g., gold, silver, copper and platinum), semiconductor (e.g., CdSe, CdS, and CdS or CdSe coated with ZnS) and magnetic (e.g., ferromagnetite) colloidal materials, as long as the nanoparticle has the ability to quench the otherwise detectable marker. Other nanoparticles useful in the practice of the invention include ZnS, ZnO, TiO$_2$, AgI, AgBr, HgI$_2$, PbS, PbSe, ZnTe, CdTe, In$_2$S$_3$, In$_2$Se$_3$, Cd$_3$P$_2$, Cd$_3$As$_2$, InAs, and GaAs. The size of the nanoparticles is preferably from about 5 nm to about 150 nm (mean diameter), more preferably from about 5 to about 50 nm, most preferably from about 10 to about 30 nm. The size of the nanoparticle is contemplated to be from about 5 to about 10 nm, or about 5 to about 20 nm, or about 5 to about 30 nm, or about 5 to about 40 nm, or about 5 to about 60 nm, or about 5 to about 70 nm, or about 5 to about 80 nm, or about 5 to about 90 nm, or about 5 to about 100 nm, or about 5 to about 110 nm, or about 5 to about 120 nm, or about 5 to about 130 nm, or about 5 to about 140 nm, or about 10 to about 20 nm, or about 10 to about 40 nm, or about 10 to about 50 nm, or about 10 to about 60 nm, or about 10 to about 70 nm, or about 10 to about 80 nm, or about 10 to about 90 nm, or about 10 to about 100 nm, or about 10 to about 110 nm, or about 10 to about 120 nm, or about 10 to about 130 nm, or about 10 to about 140 nm, or about 10 to about 150 nm. The nanoparticles may also be rods, prisms, or tetrahedra.

Thus, nanoparticles are contemplated for use in the methods which comprise a variety of inorganic materials including, but not limited to, metals, semi-conductor materials or ceramics as described in US patent application No 20030147966. For example, metal-based nanoparticles include those described herein. Ceramic nanoparticle materials include, but are not limited to, brushite, tricalcium phosphate, alumina, silica, and zirconia. Organic materials from which nanoparticles are produced include carbon. Nanoparticle polymers include polystyrene, silicone rubber, polycarbonate, polyurethanes, polypropylenes, polymethylmethacrylate, polyvinyl chloride, polyesters, polyethers, and polyethylene. Biodegradable, biopolymer (e.g. polypeptides such as BSA, polysaccharides, etc.), other biological materials (e.g. carbohydrates), and/or polymeric compounds are also contemplated for use in producing nanoparticles.

In practice, methods are provided using any suitable nanoparticle having molecules attached thereto that are in general suitable for use in detection assays known in the art to the extent and do not interfere with polynucleotide complex formation, i.e., hybridization to form a double-strand or triple-strand complex. The size, shape and chemical composition of the particles contribute to the properties of the resulting oligonucleotide-functionalized nanoparticle. These properties include for example, optical properties, optoelectronic properties, electrochemical properties, electronic properties, stability in various solutions, magnetic properties, and pore and channel size variation. The use of mixtures of particles having different sizes, shapes and/or chemical compositions, as well as the use of nanoparticles having uniform sizes, shapes and chemical composition, is contemplated. Examples of suitable particles include, without limitation, nanoparticles, aggregate particles, isotropic (such as spherical particles) and anisotropic particles (such as non-spherical rods, tetrahedral, prisms) and core-shell particles such as the ones described in U.S. patent application Ser. No. 10/034,451, filed Dec. 28, 2002 and International application no. PCT/US01/50825, filed Dec. 28, 2002, the disclosures of which are incorporated by reference in their entirety.

Methods of making metal, semiconductor and magnetic nanoparticles are well-known in the art. See, for example, Schmid, G. (ed.) Clusters and Colloids (VCH, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., *Science*, 272, 1924 (1996); Henglein, A. et al., *J. Phys. Chem.*, 99, 14129 (1995); Curtis, A. C. et al., *Angew. Chem. Int. Ed. Engl.*, 27, 1530 (1988). Preparation of polyalkylcyanoacrylate nanoparticles prepared is described in Fattal, et al., *J. Controlled Release* (1998) 53: 137-143 and U.S. Pat. No. 4,489,055. Methods for making nanoparticles comprising poly(D-glucaramidoamine)s are described in Liu, et al., *J. Am. Chem. Soc.* (2004) 126:7422-7423. Preparation of nanoparticles comprising polymerized methylmethacrylate (MMA) is described in Tondelli, et al., *Nucl. Acids Res.* (1998) 26:5425-5431, and preparation of dendrimer nanoparticles is described in, for example Kukowska-Latallo, et al., *Proc. Natl. Acad. Sci. USA* (1996) 93:4897-4902 (Starburst polyamidoamine dendrimers).

Suitable nanoparticles are also commercially available from, for example, Ted Pella, Inc. (gold), Amersham Corporation (gold) and Nanoprobes, Inc. (gold).

Also as described in US patent application No 20030147966, nanoparticles comprising materials described herein are available commercially or they can be produced from progressive nucleation in solution (e.g., by colloid reaction), or by various physical and chemical vapor deposition processes, such as sputter deposition. See, e.g., HaVashi, (1987) Vac. Sci. Technol. July/August 1987, A5(4):1375-84; Hayashi, (1987) Physics Today, December 1987, pp. 44-60; MRS Bulletin, January 1990, pgs. 16-47.

As further described in US patent application No 20030147966, nanoparticles contemplated are produced using HAuCl$_4$ and a citrate-reducing agent, using methods known in the art. See, e.g., Marinakos et al., (1999) *Adv. Mater.* 11: 34-37; Marinakos et al., (1998) *Chem. Mater.* 10: 1214-19; Enustun & Turkevich, (1963) *J. Am. Chem. Soc.* 85: 3317. Tin oxide nanoparticles having a dispersed aggregate particle size of about 140 nm are available commercially from Vacuum Metallurgical Co., Ltd. of Chiba, Japan. Other commercially available nanoparticles of various compositions and size ranges are available, for example, from Vector Laboratories, Inc. of Burlingame, Calif.

Nanoparticle Functionalized with
Structure-Switching Recognition Sequence

In other embodiments, the detectable change is created by labeling the oligonucleotides with molecules (e.g., and without limitation, fluorescent molecules and dyes) that produce detectable changes upon hybridization of the oligonucleotides on the nanoparticles. In one aspect, for example, oligonucleotides or polypeptides functionalized on nanoparticles have a marker attached to the terminus distal to the nanoparticle attachment terminus, and in the absence of association with a target, the distal terminus with the marker is positioned in proximity to the nanoparticle close enough to quench fluorescence of the marker. In one aspect, metal and semiconductor nanoparticles are known fluorescence quenchers, with the magnitude of the quenching effect depending on the distance between the nanoparticles and the fluorescent molecule. Thus, in the single-strand state, the oligonucleotides attached to the nanoparticles interact with the nanoparticles through, e.g., a hairpin structure formed by the oligonucleotide through secondary structure folding, which brings the fluorescent molecule in proximity to the nanoparticle, so that significant quenching is observed. Similarly, in the unbound state, polypeptides attached to the nanoparticles would assume a conformation that would bring the marker into proximity with the nanoparticle and the marker would be quenched. Upon polynucleotide or polypeptide complex formation due to target molecule binding via the recognition sequence, the fluorescent molecule will become spaced away from the nanoparticles, diminishing quenching of the fluorescence (FIG. 1). Useful lengths of the oligonucleotides can be determined empirically. Thus, in various aspects, metallic and semiconductor nanoparticles having fluorescent-labeled oligonucleotides or polypeptides attached thereto are used in any of the assay formats described herein.

Attaching Oligonucleotides to Nanoparticles

Nanoparticles for use in the methods provided are functionalized with an oligonucleotide, or modified form thereof, which is from about 5 to about 100 nucleotides in length. Methods are also contemplated wherein the oligonucleotide is about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all oligonucleotides intermediate in length of the sizes specifically disclosed to the extent that the oligonucleotide is able to achieve the desired result. Accordingly, oligonucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 nucleotides in length are contemplated.

In still other aspects, oligonucleotides comprise from about 8 to about 80 nucleotides (i.e. from about 8 to about 80 linked nucleosides). One of ordinary skill in the art will appreciate that methods utilize compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotide in length.

The nanoparticles, the oligonucleotides or both are functionalized in order to attach the oligonucleotides to the nanoparticles. Such methods are known in the art. For instance, oligonucleotides functionalized with alkanethiols at their 3'-termini or 5'-termini readily attach to gold nanoparticles. See Whitesides, 1995, Proceedings of the Robert A. Welch Foundation 39th Conference On Chemical Research Nanophase Chemistry, Houston, Tex., pages 109-121. See also, Mucic et al., 1996, Chem. Commun. 555-557 (describes a method of attaching 3' thiol DNA to flat gold surfaces; this method can be used to attach oligonucleotides to nanoparticles). The alkanethiol method can also be used to attach oligonucleotides to other metal, semiconductor and magnetic colloids and to the other nanoparticles listed above. Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, 1974, Chemical Technology, 4: 370-377 and Matteucci and Caruthers, 1981, J. Am. Chem. Soc., 103: 3185-3191 for binding of oligonucleotides to silica and glass surfaces, and Grabar et al., 1995, Anal. Chem., 67: 735-743 for binding of aminoalkylsiloxanes and for similar binding of mercaptoaklylsiloxanes). Oligonucleotides terminated with a 5' thionucleoside or a 3' thionucleoside may also be used for attaching oligonucleotides to solid surfaces. The following references describe other methods which may be employed to attach oligonucleotides to nanoparticles: Nuzzo et al., 1987, J. Am. Chem. Soc., 109: 2358 (disulfides on gold); Allara and Nuzzo, 1985, Langmuir, 1: 45 (carboxylic acids on aluminum); Allara and Tompkins, 1974, J. Colloid Interface Sci., 49: 410-421 (carboxylic acids on copper); Iler, The Chemistry Of Silica, Chapter 6, (Wiley 1979) (carboxylic acids on silica); Timmons and Zisman, 1965, J. Phys. Chem., 69: 984-990 (carboxylic acids on platinum); Soriaga and Hubbard, 1982, J. Am. Chem. Soc., 104: 3937 (aromatic ring compounds on platinum); Hubbard, 1980, Acc. Chem. Res., 13: 177 (sulfolanes, sulfoxides and other functionalized solvents on platinum); Hickman et al., 1989, J. Am. Chem. Soc., 111: 7271 (isonitriles on platinum); Maoz and Sagiv, 1987, Langmuir, 3: 1045 (silanes on silica); Maoz and Sagiv, 1987, Langmuir, 3: 1034 (silanes on silica); Wasserman et al., 1989, Langmuir, 5: 1074 (silanes on silica); Eltekova and Eltekov, 1987, Langmuir, 3: 951 (aromatic carboxylic acids, aldehydes, alcohols and methoxy groups on titanium dioxide and silica); Lec et al., 1988, J. Phys. Chem., 92: 2597 (rigid phosphates on metals). Additionally, any suitable method for attaching oligonucleotides onto the nanoparticle surface may be used. A particularly preferred method for attaching oligonucleotides onto a surface is based on an aging process described in U.S. application Ser. No. 09/344,667, filed Jun. 25, 1999; Ser. No. 09/603,830, filed Jun. 26, 2000; Ser. No. 09/760,500, filed Jan. 12, 2001; Ser. No. 09/820,279, filed Mar. 28, 2001; Ser. No. 09/927,777, filed Aug. 10, 2001; and in International application nos. PCT/US97/12783, filed Jul. 21, 1997; PCT/US00/17507, filed Jun. 26, 2000; PCT/US01/01190, filed Jan. 12, 2001; PCT/US01/10071, filed Mar. 28, 2001, the disclosures which are incorporated by reference in their entirety. The aging process provides nanoparticle-oligonucleotide conjugates with unexpected enhanced stability and selectivity. The method comprises providing oligonucleotides preferably having covalently bound thereto a moiety comprising a functional group which can bind to the nanoparticles. The moieties and functional groups are those that allow for binding (i.e., by chemisorption or covalent bonding) of the oligonucleotides to nanoparticles. For instance, oligonucleotides having an alkanethiol, an alkanedisulfide or a cyclic disulfide covalently bound to their 5' or 3' ends can be used to bind the oligonucleotides to a variety of nanoparticles, including gold nanoparticles.

The oligonucleotides are contacted with the nanoparticles in water for a time sufficient to allow at least some of the oligonucleotides to bind to the nanoparticles by means of the functional groups. Such times can be determined empirically. For instance, it has been found that a time of about 12-24 hours gives good results. Other suitable conditions for binding of the oligonucleotides can also be determined empirically. For instance, a concentration of about 10-20 nM nanoparticles and incubation at room temperature gives good results.

Next, at least one salt is added to the water to form a salt solution. The salt can be any suitable water-soluble salt. For instance, the salt may be sodium chloride, magnesium chloride, potassium chloride, ammonium chloride, sodium acetate, ammonium acetate, a combination of two or more of these salts, or one of these salts in phosphate buffer. Preferably, the salt is added as a concentrated solution, but it could be added as a solid. The salt can be added to the water all at one time or the salt is added gradually over time. By "gradually over time" is meant that the salt is added in at least two portions at intervals spaced apart by a period of time. Suitable time intervals can be determined empirically.

The ionic strength of the salt solution must be sufficient to overcome at least partially the electrostatic repulsion of the oligonucleotides from each other and, either the electrostatic attraction of the negatively-charged oligonucleotides for positively-charged nanoparticles, or the electrostatic repulsion of the negatively-charged oligonucleotides from negatively-charged nanoparticles. Gradually reducing the electrostatic attraction and repulsion by adding the salt gradually over time has been found to give the highest surface density of oligonucleotides on the nanoparticles. Suitable ionic strengths can be determined empirically for each salt or combination of salts. A final concentration of sodium chloride of from about 0.1 M to about 1.0 M in phosphate buffer, preferably with the concentration of sodium chloride being increased gradually over time, has been found to give good results.

After adding the salt, the oligonucleotides and nanoparticles are incubated in the salt solution for an additional period of time sufficient to allow sufficient additional oligonucleotides to bind to the nanoparticles to produce the stable nanoparticle-oligonucleotide conjugates. As will be described in detail below, an increased surface density of the oligonucleotides on the nanoparticles has been found to stabilize the conjugates. The time of this incubation can be determined empirically. A total incubation time of about 24-48, preferably 40 hours, has been found to give good results (this is the total time of incubation; as noted above, the salt concentration can be increased gradually over this total time). This second period of incubation in the salt solution is referred to herein as the "aging" step. Other suitable conditions for this "aging" step can also be determined empirically. For instance, incubation at room temperature and pH 7.0 gives good results.

The conjugates produced by use of the "aging" step have been found to be considerably more stable than those produced without the "aging" step. As noted above, this increased stability is due to the increased density of the oligonucleotides on the surfaces of the nanoparticles which is achieved by the "aging" step. An alternative "fast salt aging" process produced particles with comparable DNA densities and stability. By performing the salt additions in the presence of a surfactant, for example approximately 0.01% sodium dodecylsulfate (SDS), Tween, or polyethylene glycol (PEG), the salt aging process can be performed in about an hour.

The surface density achieved by the "aging" step will depend on the size and type of nanoparticles and on the length, sequence and concentration of the oligonucleotides. A surface density adequate to make the nanoparticles stable and the conditions necessary to obtain it for a desired combination of nanoparticles and oligonucleotides can be determined empirically. Generally, a surface density of at least 10 picomoles/cm$^2$ will be adequate to provide stable nanoparticle-oligonucleotide conjugates. Preferably, the surface density is at least 15 picomoles/cm$^2$. Since the ability of the oligonucleotides of the conjugates to hybridize with nucleic acid and oligonucleotide targets can be diminished if the surface density is too great, the surface density is preferably no greater than about 35-40 picomoles/cm$^2$. Methods are also provided wherein the oligonucleotide is bound to the nanoparticle at a surface density of at least 10 pmol/cm$^2$, at least 15 pmol/cm$^2$, at least 20 pmol/cm$^2$, at least 25 pmol/cm$^2$, at least 30 pmol/cm$^2$, at least 35 pmol/cm$^2$, at least 40 pmol/cm$^2$, at least 45 pmol/cm$^2$, at least 50 pmol/cm$^2$, or 50 pmol/cm$^2$ or more.

"Hybridization," which is used interchangeably with the term "complex formation" herein, means an interaction between two or three strands of nucleic acids by hydrogen bonds in accordance with the rules of Watson-Crick DNA complementarity, Hoogstein binding, or other sequence-specific binding known in the art. Alternatively it can mean an interaction between polypeptides as defined herein in accordance with sequence-specific binding properties known in the art. Hybridization can be performed under different stringency conditions known in the art. Under appropriate stringency conditions, hybridization between the two complementary strands or two polypeptides could reach about 60% or above, about 70% or above, about 80% or above, about 90% or above, about 95% or above, about 96% or above, about 97% or above, about 98% or above, or about 99% or above in the reactions.

In various aspects, the methods include use of two or three oligonucleotides or polypeptides which are 100% complementary to each other, i.e., a perfect match, while in other aspects, the individual oligonucleotides are at least (meaning greater than or equal to) about 95% complementary to each over the all or part of length of each oligonucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to each other.

It is understood in the art that the sequence of the oligonucleotide used in the methods need not be 100% complementary to each other to be specifically hybridizable. Moreover, oligonucleotide may hybridize to each other over one or more segments such that intervening or adjacent segments are not involved in the hybridization event (e.g., a loop structure or hairpin structure). Percent complementarity between any given oligonucleotide can be determined routinely using BLAST programs (Basic Local Alignment Search Tools) and PowerBLAST programs known in the art (Altschul et al., 1990, *J. Mol. Biol.*, 215: 403-410; Zhang and Madden, 1997, *Genome Res.*, 7: 649-656).

In one aspect, methods are provided wherein the packing density of the oligonucleotides on the surface of the nanoparticle is sufficient to result in cooperative behavior between nanoparticles and between polynucleotide strands on a single nanoparticle. In another aspect, the cooperative behavior between the nanoparticles increases the resistance of the oligonucleotide to degradation.

As used herein, "stable" means that, for a period of at least six months after the conjugates are made, a majority of the oligonucleotides remain attached to the nanoparticles and the oligonucleotides are able to hybridize with nucleic acid and oligonucleotide targets under standard conditions encountered in methods of detecting nucleic acid and methods of nanofabrication.

Each nanoparticle utilized in the methods provided has a plurality of oligonucleotides attached to it. As a result, each nanoparticle-oligonucleotide conjugate has the ability to hybridize to a second oligonucleotide that is conjugated to a fluorophore detectably distinct from the fluorophore present on the first nanoparticle-oligonucleotide conjugate and functionalized on a second nanoparticle, and when present, a free oligonucleotide, having a sequence sufficiently complementary. In one aspect, methods are provided wherein each nanoparticle is functionalized with identical oligonucleotides, i.e., each oligonucleotide attached to the nanoparticle has the same length and the same sequence. In other aspects, each nanoparticle is functionalized with two or more oligonucleotides which are not identical, i.e., at least one of the attached oligonucleotides differ from at least one other attached oligonucleotide in that it has a different length and/or a different sequence.

The term "oligonucleotide" or "polynucleotide" includes those wherein a single sequence is attached to a nanoparticle, or multiple copies of the single sequence are attached. For example, in various aspects, an oligonucleotide is present in multiple copies in tandem, for example, two, three, four, five, six, seven eight, nine, ten or more tandem repeats.

Alternatively, the nanoparticle is functionalized to include at least two oligonucleotides having different sequences with the proviso that each oligonucleotide is labeled with a detectably distinct marker. As above, the different oligonucleotide sequences are in various aspects arranged in tandem and/or in multiple copies. Alternatively, the oligonucleotides having different sequences are attached directly to the nanoparticle. In methods wherein oligonucleotides having different sequences are attached to the nanoparticle, aspects of the methods include those wherein the different oligonucleotide sequences hybridize to different regions on the same polynucleotide.

The oligonucleotides on the nanoparticles may all have the same sequence or may have different sequences that hybridize with different portions of the polynucleotide attached to another nanoparticle. When oligonucleotides having different sequences are used, each nanoparticle may have all of the different oligonucleotides attached to it or the different oligonucleotides are attached to different nanoparticles. Alternatively, the oligonucleotides on each of the nanoparticles may have a plurality of different sequences, at least one of which must hybridize with a portion of the polynucleotide on a second nanoparticle.

Nano-Flare Technology

In an aspect of the present invention, an oligonucleotide or polypeptide containing the recognition sequence in the binding moiety that is attached to the nanoparticle as described herein. "Recognition sequence" as used herein is understood to mean a sequence that is partially or completely complementary to a target molecule of interest.

Figure 2:
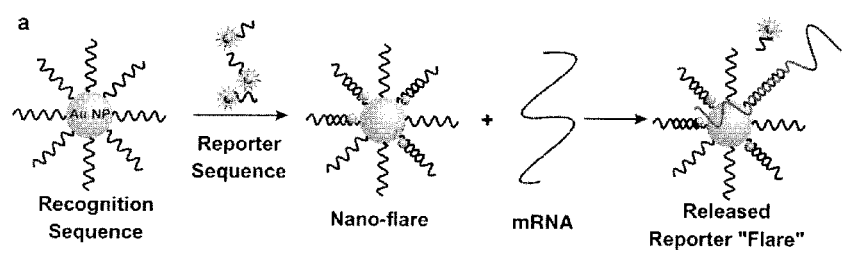
FIG. 2 shows nano-flares for mRNA detection and quantification.

The nanoparticle with attached oligonucleotide binding moiety that contains a recognition sequence is initially associated with a reporter sequence. As used herein, a "reporter sequence" is understood to mean a sequence that is partially or completely complementary and therefore able to hybridize to the binding moiety and its recognition sequence. The reporter sequence is labeled as discussed herein above, and is also referred to as a nano-flare. Further, the reporter sequence is in various aspects comprised of fewer, the same or more bases than the recognition sequence, such that binding of the recognition sequence in the binding moiety to its target molecule causes release of the hybridized reporter sequence, thereby resulting in a detectable and measurable change in the label attached to the reporter sequence (FIG. 2).

In one specific aspect, nanoparticles functionalized with a recognition sequence for a specific target mRNA are hybridized with a short complementary Cy5 labeled reporter polynucleotide having a reporter sequence and where the fluorescence of the Cy5 portion is quenched when hybridized to the recognition sequence on the nanoparticle. This reporter sequence is also capable of being displaced by the target mRNA. Upon displacement, the Cy5 portion is no longer quenched and fluoresces, allowing for detection and quantification of a fluorescent signal, which is correlated to the amount of target sequence hybridized to the recognition sequence with concomitant displacement of the reporter sequence.

Nano-flares take advantage of the unique optical properties of gold nanoparticles (Au NPs). Au NPs quench fluorescence with a greater efficiency (Dubertret et al., 2001, Nat. Biotechnol. 19: 365-370) and over greater distances (Dulkeith et al., 2005, Nano Lett. 5: 585-589) than molecular quenchers. Likewise, all other types of nanoparticles described herein may be used as long as they are able to quench the detectable marker of an attached binding moiety.

Those of skill in the art are able to determine relative melting temperatures and/or hybridization conditions in the case of in vitro studies without undue experimentation that will facilitate reporter binding to the recognition sequence in the absence of the target molecule while resulting in displacement of said reporter sequence in the presence of said target molecule.

The invention is illustrated by the following examples, which are not intended to be limiting in any way.

Examples

Example 1

This example is meant to demonstrate that fluorescently labeled oligonucleotide-modified gold nanoparticle agents can be used to detect intracellular molecule targets. As a proof-of-concept, it is demonstrated that intracellular detection of mRNA targets in two cell-types using fluorescently labeled oligonucleotide-modified gold nanoparticles is highly effective. These agents readily enter the cells and produce a fluorescent signal that can easily be read using both fluorescent microscopy and flow-cytometry.

Specifically, 13 nm gold nanoparticles were modified with several different sequences that are terminated on one end with a thiol moiety, on the other end with a fluorescent dye, and contain a structure-switching recognition sequence. In the absence of the target, the dye molecule is in close proximity with the gold nanoparticle surface, which leads to quenching and no fluorescent signal. In the presence of the target, the dye molecule is separated from the gold nanoparticle surface and a fluorescent signal is observed (FIG. 1).

Au NPs were functionalized with thiolated oligonucleotides containing an 18-base recognition element to a specific RNA transcript (FIG. 1) via gold thiol bond formation (Love et al., 2005, Chem. Rev. 105: 1103-1169). Oligonucleotide functionalized Au NPs were then allowed to hybridize with short cyanine (Cy5) dye-terminated reporter sequences capable of acting as "flares" when displaced by a longer target or target region (FIG. 1). In the bound state, the Cy5 fluorescence of the reporter strand is quenched due to proximity to the Au NP surface. In the presence of a target, the flare strand is displaced and liberated from the Au NP by forming the longer and more stable duplex between the target and the oligonucleotide-modified Au NP.

Example 2

To further exemplify the use of the gold nanoparticles' ability to enter cells and detect intracellular target molecules, in vitro cell culture experiments were carried out.

C166 mammalian cells that stably express the enhanced green fluorescence protein were maintained in Dulbecco's Modified Eagles Medium with 10% serum at 37° C. and 5% $CO_2$ and dosed with fluorescently labeled oligonucleotide-modified gold nanoparticle agents that target the enhanced green fluorescence (EGFP) protein mRNA. SKBR3 human breast cancer (vide infra) and C166 mouse endothelial cells were obtained from the American Tissue Culture Collection (ATCC) and were grown in McCoy's 5A Medium and Dulbecco's Modified Eagles medium (DMEM), respectively, with 10% heat inactivated fetal bovine serum and maintained at 37° C. in 5% $CO_2$. Cells were seeded in 6 or 24 well plates and grown for 1-2 days prior to treatment. On the day of treatment, the cells were approximately 50% confluent. The media was replaced with fresh media containing the functionalized Au NPs.

Control experiments were performed with particles containing targeting regions for the anthrax RNA, which is not present in mammalian cells. After transfection for 16 hour, these EGFP-expressing cells treated with the EGFP targeting probes displayed a bright fluorescent signal, much greater than the signal observed in the control particles. As a further control experiment, the particles were tested in C166 cells that do not express EGFP and hence do not contain the EGFP mRNA target. In these experiments neither probe was found to signal once inside the cells, thus confirming that fluorescently labeled oligonucleotide-modified gold nanoparticle agents can be used to detect specific intercellular molecules targets.

The probe entry into the cells was confirmed using inductivity-coupled plasma mass spectrometry in order to quantify the uptake and also rule out any sequence dependent uptake effects. These data confirm that after a typical experiment, the cells contain approximately 100,000 gold nanoparticles, and that the C166 cells take-up a similar number of gold nanoparticles regardless of the recognition sequence contained in the oligonucleotides.

Example 3

The fluorescently labeled oligonucleotide-modified gold nanoparticle agents were further examined for their oligonucleotide loading and fluorescence signaling ability. The results of these experiments confirm that each gold nanoparticle is functionalized with approximately 60 fluorescent oligonucleotides that contain the recognition sequence. Furthermore, when a 1 nM solution of the various oligonucleotide-modified gold nanoparticle agents were digested in a KCN solution, they all displayed a nearly identical florescence. Taken together this characterization data indicates that in the absence of target, the fluorescently labeled oligonucleotide-modified gold nanoparticle agents display an identical fluorescence signal, further confirming that the intracellular signaling observed was caused by a specific intracellular binding event.

The detection of endogenous genes is of particular importance for drug discovery and genetic research. Thus, gold nanoparticles were prepared that can be used to sense the presence of the cancer gene survivin. These particles, when compared control sequences, again display a bright fluorescent signal from inside survivin expressing A549 lung cancer cells. These results indicate that the described fluorescently labeled oligonucleotide-modified gold nanoparticle agents can be used to directly read out the presence of a native mRNA target.

The fluorescence signals that were observed can alternatively be detected in large populations of the treated cells using a simple, bench-top flow cytometer instrument. These experiments again highlight the very efficient uptake efficiency that is observed for these fluorescently labeled oligonucleotide-modified gold nanoparticle agents, and also that nearly all cells in a given sample show strong signal indicating the presence of an intracellular mRNA target. Here, 1000 cell counts were plotted as a function of their fluorescence intensity using a Guava Easy Cyte flow cytometer and the instruments software. In these experiments it was observed that a dramatic shift in the fluorescence of the population of the survivin expressing A549 cells was seen when they were treated with the survivin targeting fluorescently labeled oligonucleotide-modified gold nanoparticle agents, relative to those treated with the control anthrax targeting agents. The results indicate that when coupled to flow-cytometry, fluorescently labeled oligonucleotide-modified gold nanoparticle agents are well-suited for sorting large populations of cells.

Also compared was the efficiency of the particle with a conventional quencher-fluorophore oligonucleotide sequence that has been transfected into the cells with the Lipofectamine 2000 formulation. Under the analogous conditions where our particles showed dramatic signaling ability, these formulations show a negligible signaling ability. Even when their concentration was increased 10 times, they showed little or no signal, thus proving that under these conditions, the nanoparticles outperform a conventional quencher-fluorophore oligonucleotide probe.

Taken in sum, the foregoing examples show that:

1) The gold nanoparticles assist in the intracellular delivery of a fluorophore containing oligonucleotide that is capable of detecting a target.

2) These fluorescently labeled oligonucleotide-modified gold nanoparticle agents can be used to detect both endogenous and exogenous intracellular targets.

3) The fluorescent signal that indicates the presence of the specific mRNA target can be read by either a fluorescent microscope or a flow-cytometer.

4) The efficient uptake of these agents and their high signaling ability makes them well suited for sorting large cell populations.

5) The efficient uptake of these agents and their high signaling ability surpasses conventional quencher-fluorophore oligonucleotide probe under the conditions studied.

6) The principles can be extended to other structure-switching recognition sequences such as nucleic acid aptamers and peptides.

Additional fluorescently labeled aptamer-containing particle probes that target the molecule adenosine triphosphate (ATP) are also contemplated by the present invention.

The present invention also contemplates the ability to simultaneously detect multiple intracellular targets, and quantify their intracellular concentrations in real time. The principles can be applied to real-time monitoring cell function in higher organisms.

Example 4

Nano-flares have been prepared using 13 nm Au NPs, since this size particle is an efficient quencher, can be densely functionalized with oligonucleotides (Mirkin et al., 1996, *Nature* 382: 607-609), and does not efficiently scatter visible light, which is important for designing optical probes with minimal interference.

Au NPs were functionalized with thiolated oligonucleotides containing a recognition element to a specific RNA transcript (FIG. 2) via gold thiol bond formation (Love et al., 2005, *Chem. Rev.* 105: 1103-1169). Oligonucleotides were synthesized on an Expedite 8909 Nucleotide Synthesis System (ABI) using standard solid-phase phosphoramidite methodology. Bases and reagents were purchased from Glen Research. Oligonucleotides were purified by reverse-phase high performance liquid chromatography (HPLC). To prepare nano flare probes, citrate-stabilized gold nanoparticles (13±1 nm) were prepared using published procedures (Frens, G., 1973, *Nature—Physical Science* 241: 20-22. Thiol-modified oligonucleotides were added to 13±1 nm gold colloids at a concentration of 3 nmol of oligonucleotide per 1 mL of 10 nM colloid and shaken overnight. After 12 hours, sodium dodecylsulfate (SDS) solution (10%) was added to the mixture to achieve a 0.1% SDS concentration. Phosphate buffer (0.1 M; pH 7.4) was added to the mixture to achieve a 0.01 M phosphate concentration, and six aliquots of sodium chloride solution (2.0 M) were then added to the mixture over an eight-hour period to achieve a final sodium chloride concentration of 0.15 M. The mixture was shaken overnight to complete the functionalization process. The solution containing the functionalized particles was centrifuged (13,000 rpm, 20 min) and resuspended in phosphate buffered saline (PBS; 137 mM NaCl, 10 mM Phosphate, 2.7 mM KCl, pH 7.4, Hyclone) three times to produce the purified Au NPs used in all subsequent experiments. The concentration of the particles was determined by measuring their extinction at 524 nm ($\epsilon=2.7\times 10^8$ L mol$^{-1}$ cm$^{-1}$). Purified, oligonucleotide functionalized Au NPs were suspended to a concentration of 10 nM in PBS (PBS; 137 mM NaCl, 10 mM Phosphate, 2.7 mM KCl, pH 7.4, Hyclone) containing 100 nM of the complementary Cy5 labeled reporter sequence. The mixture was heated to 70° C., slowly cooled to room temperature, and stored in the dark for at least 12 hours to allow hybridization. Particles were filter sterilized using a 0.2 µm acetate syringe filter (GE Healthcare). The oligonucleotide sequences that were used are as follows:

Recognition Sequence:
(SEQ ID NO. 1)
5'-CTT GAG AAA GGG CTG CCA AAA AA-SH-3'

Reporter Sequence:
(SEQ ID NO. 2)
3'-CCC GAC GGT T-Cy5-5'

Target Region:
(SEQ ID NO. 3)
3'-GAA CTC TTT CCC GAC GGT-5'

Nano-flare probes or molecular beacons were diluted to a concentration of 1 nM in PBS containing 0.1% Tween 20 (Sigma) and treated with a complementary target (target concentration, 1 µM). The fluorescence spectra were recorded on a Jobin Yvon Fluorolog FL3-22 exciting at 633 nm and measuring emission from 650 to 750 nm in 1 nm increments. Oligonucleotide functionalized Au NPs were then allowed to hybridize with short cyanine (Cy5) dye-terminated reporter sequences capable of acting as "flares" when displaced by a longer target or target region. In the bound state, the Cy5 fluorescence of the reporter strand is quenched due to proximity to the Au NP surface. In the presence of a target, the flare strand is displaced and liberated from the Au NP by forming the longer and more stable duplex between the target and the oligonucleotide-modified Au NP.

Testing the nano-flare design using synthetic complementary targets demonstrates that the probes respond with a 3.8-fold increase in fluorescence signal upon target recognition and binding. In contrast, the signal does not change in the presence of a non-complementary target, and is of comparable magnitude to background fluorescence. These results thus demonstrate that nano-flares are efficient at signaling the presence of a specific target.

Example 5

Having established the signaling ability of nano-flare probes with synthetic targets, their ability to enter, visualize and detect RNA targets in live cells was investigated. Nano-flares were designed to incorporate a complementary region for the survivin transcript, a target that has received significant attention due to its potential use in cancer therapeutics and diagnostics (Altieri et al., 2003, *Oncogene* 22: 8581-8589). The SKBR3 cell line (human breast cancer), which expresses a high number of survivin transcripts (Peng et al., 2005, *Cancer Res.* 65: 1909-1917), was used as a model to test survivin-targeting nano-flares. The survivin recognition and reporter sequences are as shown above (SEQ ID NO. 1 and SEQ ID NO. 2). As a control, a second probe containing a non-complementary sequence was prepared. The non-complementary probe was designed and determined to have similar background fluorescence, melting properties, and signaling ability as the survivin probe. The survivin control probe oligonucleotide sequence was:

Control particle recognition sequence:
(SEQ ID NO. 4)
5'-CTA TCG CGT ACA ATC TGC AAA AA-SH-3'

Control particle reporter sequence:
(SEQ ID NO. 5)
3'-GCA TGT TAG ACG T-Cy5-5'

Survivin molecular beacon:
(SEQ ID NO. 6)
5'-Cy5-CGA CGG AGA AAG GGC TGC CAC GTC G dabcyl-3'

Control molecular beacon,
(SEQ ID NO. 7)
5'-Cy5-CGA CGT CGC GTA CAA TCT GCC GTC G-dabcyl-3'

Cells were cultured on glass microscope cover slips, incubated with nano-flares, and imaged using scanning confocal microscopy. Specifically, cells were grown on glass coverslips placed at the bottom of 6 well tissue culture plates. After 1 day, the media was replaced with media containing nano-flares (particle concentration, 125 pM). After 6 hours of treatment, the media was replaced, and the cells were cultured for an additional 12 hours. The coverslips were removed, washed with PBS, and fixed to a chamber filled with PBS mounted on a glass slide. All images were obtained with a Zeiss 510 LSM at 63× magnification using a 633 nm HeNe laser excitation source.

SKBR3 cells treated with survivin nano-flares were highly fluorescent as compared to those treated with the non-complementary controls. To further confirm that this signaling is consistent with the presence of survivin, a C166 cell-line (mouse endothelial) was used as a control since it does not contain the human survivin transcript. C166 cells were treated with both the survivin and control probes. In this case, no distinguishable difference in the fluorescence of the cells was observed after treatment. These imaging results were consistent with reverse transcriptase PCR (RT-PCR) measurements (vide infra).

In order to quantify the intracellular signaling of the nano-flares, cells treated with probes were examined using analytical flow-cytometry. Additionally, flow cytometry allows one to collect fluorescence data for a large population of cells. This eliminates variations and experimental artifacts that can be observed using techniques such as fluorescence imaging which only permit the examination of a small sample of cells. Cells were treated with nano-flares as described above (particle concentration, 10 nM). Molecular beacon probes (SEQ ID NO. 6 and SEQ ID NO. 7) were delivered to cells using Lipofectamine 2000 (Invitrogen). After treatment, cells were detached from culture flasks using trypsin. Flow cytometry was performed using a DakoCytomation CyAn, exciting at 635 nm.

Cell-lines transfected with nano-flares showed uniform single populations of fluorescent cells, consistent with the greater than 99% cell penetration that we observe when transfecting antisense particles (Rosi et al., Science 312: 1027-1030). Flow-cytometry revealed that SKBR3 cells treated with survivin nano-flares were highly fluorescent and 2.5 times more fluorescent than the population treated with non-complementary controls. For comparison, in C166 cell models, both probes resulted in a similar low fluorescent signal. These flow cytometry experiments are in excellent agreement with confocal imaging and demonstrate the uniform cellular internalization and intracellular signaling of the nano-flares.

Experiments then were designed to understand the unique properties of these probes in the context of intracellular detection experiments. First, the intracellular performance of nano-flares was compared with a molecular beacon reporter delivered using Lipofectamine, a commercial transfection agent (Peng et al., 2005, Cancer Res. 65: 1909-1917; Nitin et al., 2004, Nucleic Acids Res. 32: e58). Molecular beacons and nano-flares were introduced to SKBR3 cells (transfection concentration, 10 pM) and their signal abilities were studied using flow cytometry. Cells treated with survivin nano-flares produced 55 times greater fluorescence signal than those treated with survivin molecular beacon probes transfected at the same concentration. Fluorescence measurements outside of the cell culture indicate that each nano-flare probe contains approximately 10 fluorophores and therefore could be expected to potentially have a 10 times greater signal than the molecular beacon at equal probe concentrations. The larger than expected intracellular fluorescence suggests that nano-flares are internalized more rapidly or to a greater extent than the molecular beacon probes.

Next, molecular beacons were transfected at high concentration (0.5 nM) to achieve an intracellular fluorescence signal to that observed with the nano-flares. The background fluorescence contributed by the non-complementary probes was compared (both molecular beacon and nano-flare). The fluorescence of the non-complementary molecular beacon probe is significantly greater than that of the non-complementary nano-flare. Since the difference between the background and signal is critical for accurate target detection, the lower background of nano-flares provides an important advantage when detecting intracellular targets.

To probe how enzymatic degradation leads to non-specific signaling, nano-flares were incubated with the endonuclease DNAse I (0.38 mg/L, a concentration significantly greater than what would be found in a cellular environment), and measured the rate of degradation by monitoring the increase in fluorescence signal as a function of time. Nano-flare probes were diluted to a concentration of 2.5 nM in PBS (pH 7.0), 0.25 mM $MgCl_2$ and 50 mg/L Bovine Serum Albumin (Fischer Scientific). Bovine Pancreatic DNase I (United States Biochemical) was added immediately before reading (concentration, 0.38 mg/L). All experiments were preformed on a Photal Otsuka Electronics FluoDia T70 with excitation at 620 nm and emission at 665 nm. Molecular beacons were tested in an analogous manner at a concentration of 25 nM. The approximate rates of degradation under these experimental conditions were determined from the slope of the linear region of the degradation curves (Rizzo et al., 2002 Molecular and Cellular Probes 16: 277-283.

The results of the assay reveal that the nano-flare is degraded at a normalized rate of 0.275 nmol min$^{-1}$ under these conditions. In comparison, a molecular beacon is degraded at a normalized rate of 1.25 nmol min$^{-1}$, approximately 4.5 times more rapidly than the nano-flare. Since nuclease activity leads to increased background fluorescence in a conventional probe, the reduced nuclease activity of the nano-flares leads to a system with lower background signal.

Example 6

To demonstrate an application where the cellular entry, elevated signaling, and low background of the nano-flare translate into a high sensitivity for changes in intracellular amounts of RNA, siRNA knockdown experiments were conducted to reduce the levels of survivin RNA transcripts in the SKBR3 cell models. siRNA against human survivin (Santa Cruz) was delivered to cells using Lipofectamine 2000 (Invitrogen) when cells were approximately 50% confluent (siRNA concentrations, 20, 40, and 80 nM). After 24 hours, the media was changed with media containing the nano-flare probes (particle concentration, 50 pM). After 6 hours, the cells were washed and fresh media was added. Cells were cultured for an additional 12 hours and analyzed using flow cytometry.

Figure 3:
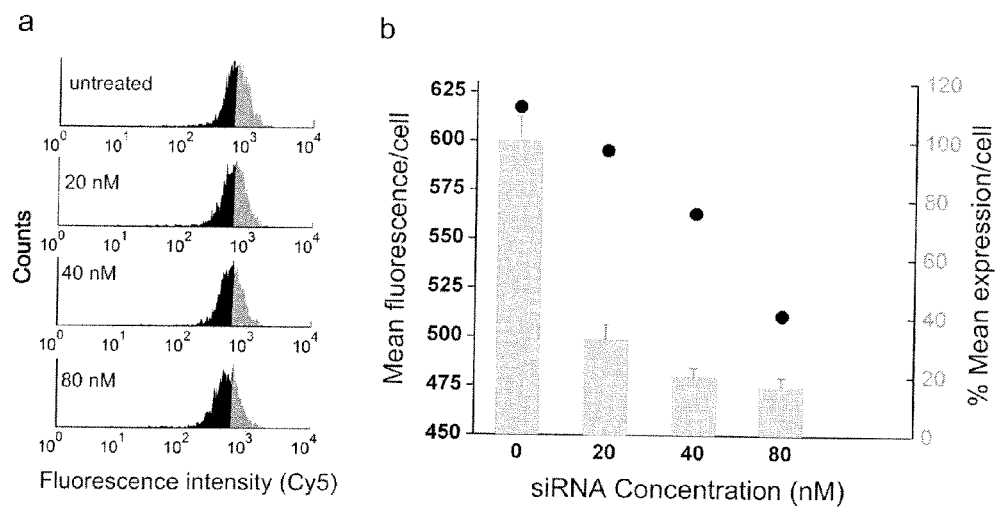
FIG. 3 describes quantification of survivin knockdown using nano-flares. (a) Flow cytometry data collected on siRNA treated SKBR3 cells. (b) Plot of mean fluorescence (black circles) and survivin expression (grey bar-graph) as a function of siRNA concentration.

Cells were initially treated with siRNA against survivin, and the intracellular RNA levels were quantified using nano-flares and flow cytometry. An siRNA concentration-dependent shift in the fluorescence of the cell population was observed as a function of the concentration of siRNA added to the cell culture (FIG. 3a). The siRNA concentration is given in the graph to the left of the histogram. In the untreated sample, half of the population exhibiting equal or greater fluorescence than the mean is shaded grey. Treated samples show a smaller fraction of the cell population exhibiting the mean fluorescence (declining grey, increasing black). To confirm that this shift was commensurate with a decrease in the number of survivin transcripts, RT-PCR measurements were conducted on samples treated with the same concentrations of siRNA. Cells were counted using a Guava EasyCyte Mini (Guava Technologies). Total RNA was isolated from the cell using an RNeasy Plus Kit (Qiagen) following the manufacturers protocol. During the cell lysis step, $5 \times 10^7$ copies of Enhanced Green Fluorescent Protein (EGFP) RNA were added to each sample to account for RNA loss during isolation and purification. To generate RNA standard curves for qRT-PCR, the fragments of RNA to be quantified were generated from the appropriate cellular RNA. Using PCR and primers containing a T7 promoter site, we converted the fragments into transcription compatible sequences (DNA→RNA). The transcripts were purified using the MEGAclear kit (Ambion) following the manufacturer's protocol. RNA concentration was measured using the Ribogreen RNA quantification kit (Invitrogen), and a dilution series of stock RNA was used to generate a standard curve. Primers were:

EGFP Forward
(SEQ ID NO. 8)
5'-TCT TCT TCA AGG ACG ACG GCA ACT-3'

EGFP Reverse
(SEQ ID NO. 9)
5'-TGT GGC GGA TCT TGA AGT TCA CCT-3'

T7 EGFP Forward
(SEQ ID NO. 10)
5'-TGC ATA ATA CGA CTC ACT ATA GGG AGA TCT TCA AGG ACG ACG GGC AAC T-3'

Survivin Forward
(SEQ ID NO. 11)
5'-ATG GGT GCC CCG ACG TTG-3'

-continued

Survivin Reverse (SEQ ID NO. 12)

5'-AGA GGC CTC AAT CCA TGG-3'

T7 Survivin Forward (SEQ ID NO. 13)

5'-TGC ATA ATA CGA CTC ACT ATA GGG AGA TGG GTG CCC CGA CGT TG-3'

Quantitative-PCR and analysis were preformed using LightCycler RNA master SYBR green kits (Roche Applied Sciences) according to the manufacturer's recommendation. Reverse transcription was allowed to proceed at 61° C. for 20 minutes, followed by 45 amplification cycles (95° C., 5 sec; 54° C., 15 sec; 72° C., 20 sec), and target gene RNA was normalized to the standard curves generated. All reactions were done in triplicate.

The linear decrease in the fluorescence signal within the population of cells was in agreement with the decrease in the number of survivin RNA copies as determined by RT-PCR measurements (FIG. 3b). Taken together, these results indicate that the nano-flares are sensitive to changes in the number of intracellular transcripts. The RT-PCR was conducted in triplicate, and the error bars shown above are the standard deviations of those measurements.

A new class of intracellular probe termed "nano-flares" has been developed. Nano-flares are novel and potentially very useful since they are the only probe that combines cellular transfection, enzymatic protection, RNA detection and quantification, and mRNA visualization. In addition to their demonstrated use in the context of siRNA knockdown experiments, nano-flares are contemplated to be useful in other areas such as cell sorting, gene profiling, and real-time drug testing. Finally, given the ability of these materials to also act as gene regulation agents (Rosi et al., 2006, *Science* 312: 1027-1030; Seferos et al., 2007, *Chem Bio Chem* 8: 1230-1232), these probes are contemplated to easily adapted to simultaneously transfect, control and visualize gene expression in real-time.

In summary, these results demonstrate:

1) Gold nanoparticles assist in the intracellular delivery of a fluorophore-containing oligonucleotide that is capable of detecting a target.

2) These fluorescently labeled oligonucleotide-modified gold nanoparticle agents can be used to detect, visualize, and quantify intracellular targets.

3) The fluorescent signal that indicates the presence and quantity of specific mRNA targets can be transduced into a readable measure.

4) The efficient uptake of these agents, and their high signaling ability, and low toxicity makes them well suited for distinguishing cell populations.

5) The efficient uptake of these agents, and their high signaling ability surpasses conventional quencher-fluorophore oligonucleotide probes under the conditions studied.

6) The principles can be extended to other structure-switching recognition sequences such as nucleic acid aptamers and peptides.

The present invention contemplates that use of the probes will lead to the ability to simultaneously detect multiple intracellular targets, and quantify their intracellular concentrations in real-time. The principles are also contemplated to be applied to real-time monitoring of cell function in higher organisms, and used to concurrently deliver therapeutics while simultaneously monitoring their efficacy.

What is claimed is:

1. A method of determining the intracellular concentration of a target polynucleotide comprising the step of contacting the target polynucleotide with a nanoparticle under conditions that allow association of the target polynucleotide with the nanoparticle, said nanoparticle comprising a binding moiety polynucleotide specific for said target polynucleotide, said binding moiety polynucleotide labeled with a marker, wherein the association of the target polynucleotide and the nanoparticle results in detectable change in the marker, wherein the change in the detectable marker is proportional to the intracellular concentration of said target polynucleotide, said binding moiety polynucleotide is covalently attached to said nanoparticle and said marker is a label attached to a polynucleotide hybridized to said binding moiety polynucleotide, wherein association of said binding moiety polynucleotide with said target polynucleotide releases said hybridized polynucleotide and said marker is detectable after release.

2. The method of claim 1 wherein the binding moiety polynucleotide is DNA.

3. The method of claim 1 wherein the binding moiety polynucleotide is RNA.

4. The method of claim 1 wherein said label attached to said polynucleotide is quenched when said polynucleotide with said label is hybridized to said binding moiety polynucleotide.

5. The method of claim 1 wherein said binding moiety polynucleotide comprises a marker which is a detectable label, wherein said marker is detectable only when said binding moiety polynucleotide is associated with the target polynucleotide.

6. The method of claim 5 wherein said marker is quenched when said binding moiety polynucleotide is not associated with said target polynucleotide.

7. The method of claim 1 wherein said nanoparticle comprises a multiplicity of binding moiety polynucleotides.

8. The method of claim 7 wherein the binding moiety polynucleotides specifically associate with one target polynucleotide.

9. The method of claim 7 wherein the binding moiety polynucleotides specifically associate with more than one target polynucleotide.

* * * * *

UNITED STATES PATENT AND TRADEMARK OFFICE
CERTIFICATE OF CORRECTION

PATENT NO.        : 8,507,200 B2                                       Page 1 of 1
APPLICATION NO. : 12/526560
DATED             : August 13, 2013
INVENTOR(S)       : Mirkin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 752 days.

Signed and Sealed this

Fifteenth Day of September, 2015

Michelle K. Lee
*Director of the United States Patent and Trademark Office*